United States Patent [19]

Donofrio et al.

[11] Patent Number: 5,723,588
[45] Date of Patent: Mar. 3, 1998

[54] PROTEIN-ENRICHED THERMOPLASTICS

[75] Inventors: David A. Donofrio, Scotts Valley; Erwin R. Stedronsky, La Jolla, both of Calif.

[73] Assignee: Protein Polymer Technologies, Inc., San Diego, Calif.

[21] Appl. No.: 89,862

[22] Filed: Jul. 9, 1993

Related U.S. Application Data

[63] Continuation-in-part of Ser. No. 609,716, Nov. 6, 1990, which is a continuation-in-part of Ser. No. 269,429, Nov. 9, 1988, abandoned, which is a continuation-in-part of Ser. No. 114,618, Oct. 29, 1987, Pat. No. 5,243,038, which is a continuation-in-part of Ser. No. 927,298, Nov. 4, 1986, abandoned.

[51] Int. Cl.$^6$ .......................... C07K 17/04; C07K 17/08
[52] U.S. Cl. .................................. 530/817; 530/815
[58] Field of Search ........................ 530/815, 817, 530/810, 812; 424/419, 486, 487; 525/54.1

[56] References Cited

U.S. PATENT DOCUMENTS 4,617,271 10/1986 Nambu ................................. 435/180

FOREIGN PATENT DOCUMENTS 57-108010 7/1982 Japan.

OTHER PUBLICATIONS

Dale and McBennett, "Stability of High–Temperature Enzymes", *ACS Symp. Ser.*, 498:136–152 (1992).
Finkelstein & Reva, "A Search for the Most Stable Folds of Protein Chains", *Nature*, 351:497–499 (1991)
Goodenough and Jenkins, "Protein Engineering to Change Thermal Stability for Food Enzymes", *Biochem. Soc. Trans*, 19:655–662 (1991).
Lee and Lee, "Thermal Stability of Proteins in the Presence of Poly(ethylene glycols)", *Biochemistry*, 26:7813–7819 (1987).
MacLeod et al., "Stabilization of Proteins to Heat", *Research Disclosure*, 244:380 (1984).
Matthews et al., "Enhanced Protein Thermostability from Site–directed Mutations that Decrease the Entropy of Unfolding", *Proc. Natl. Acad. Sci. USA*, 84:6663–6667 (1987).
Ponnuswamy et al., "Amino Acid Composition and Thermal Stability of Proteins", *Int. J. Biol. Macromol.*, 4:186–190 (1982).
Santoro et al., "Increased Thermal Stability of Proteins in the Presence of Naturally Occurring Osmolytes", *Biochemistry*, 31:5278–5283 (1992).
Wampler et al., "Computational Approaches to Modeling and Analyzing Thermostability in Proteins", *ACS Symp. Ser.*, 498:153–173 (1992).
Wood and Gadow, "Immobilisation of Antibodies and Antigens on Macro Solid Phases—A Comparison Between Adsorptive and Covalent Binding", *J. Clin. Chem. Clin. Biochem.*, 21:789–797 (1983).
Wozniak et al., "Crystallographic and Genetic Approaches Toward the design of Proteins of Enhanced Thermostability", *Crystallogr. Model Methods Mol. Des.*, pp. 80–94, Ed. Bugg and Ealick, NY, NY (1990).

*Primary Examiner*—Mindy B. Fleisher
*Assistant Examiner*—Nancy T. Vogel
*Attorney, Agent, or Firm*—Bertram I. Rowland

[57] ABSTRACT

Thermoplastics interdispersed with a variety of functional thermostable polypeptides, including proteins, and methods of making such thermoplastics are provided. The disclosure demonstrates that certain polypeptides can retain functional activity through exposure to plastic thermomolding. The polypeptides are exposed to the heating and molding/extrusion/casting process and are hence present on the formed plastic surface and at a depth below the plastic surface. The polypeptides contained in the disclosed compositions retain functional properties or binding specificities through the heating and molding/extrusion/casting processes. Preferred thermostable polypeptides used in the disclosed compositions include silk-like protein polymers, particularly ProNectin®F. The disclosed methods and compositions find use in many applications where plastics containing functional thermostable polypeptides are desired, in particular, cell cultureware.

10 Claims, 5 Drawing Sheets

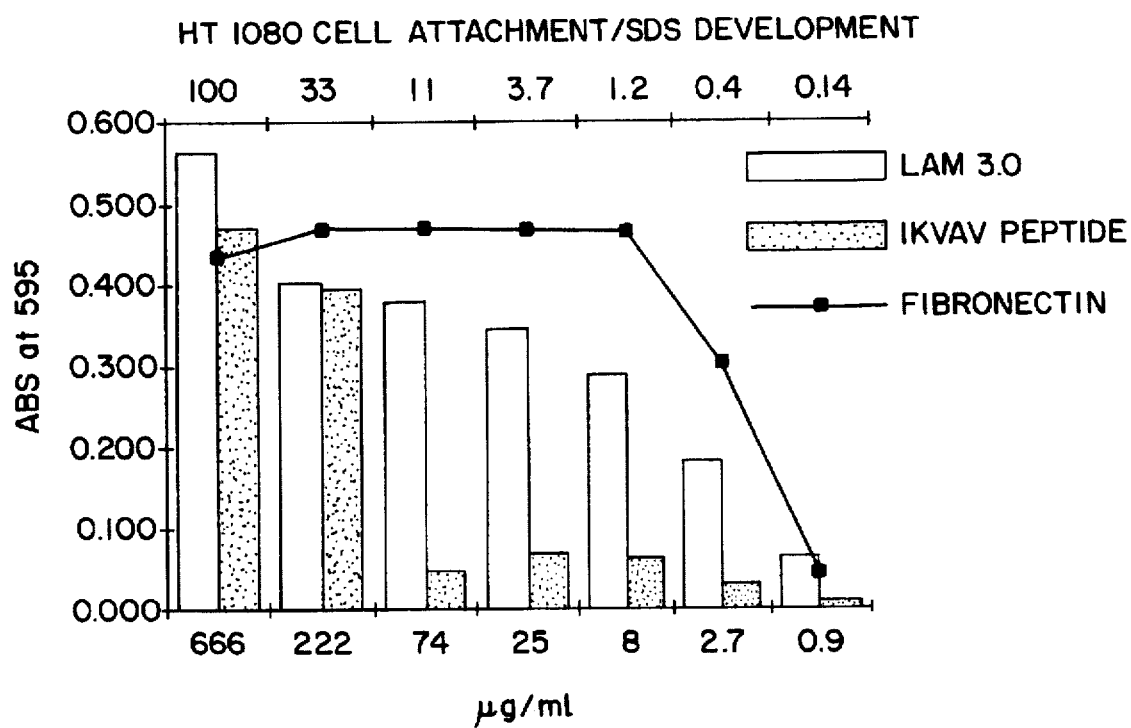

PC12 Cells after 1 day in nerve growth factor

Substrate: Uncoated polystyrene

Magnification= 400 x

PC12 Cells after 1 day in nerve growth factor

Substrate: Polylysine coated polystyrene

Magnification= 400 x

PC12 Cells after 1 day in nerve growth factor

Substrate: Collagen type I coated polystyrene

Magnification= 400 x

PC12 Cells after 1 day in nerve growth factor

Substrate: Fibronectin coated polystyrene

Magnification= 400 x

PC12 Cells after 1 day in nerve growth factor

Substrate: IKVAV peptide coated polystyrene

Magnification= 400 x

PC12 Cells after 1 day in nerve growth factor

Substrate: Laminin coated polystyrene

Magnification= 400 x

PC12 Cells
after 1 day in
nerve growth factor

Substrate:
SLPL3.0 coated
polystyrene

Magnification= 400 x

PC12 Cells
after 1 day in
nerve growth factor

Substrate:
Laminin coated
polystyrene

Magnification= 400 x

PROTEIN-ENRICHED THERMOPLASTICS

CROSS-REFERENCE TO RELATED APPLICATIONS

This Application is a continuation-in-part of application Ser. No. 609,716 filed Nov. 6, 1990, which is a continuation-in-part of application Ser. No. 269,429 filed Nov. 9, 1988, now abandoned which is a continuation-in-part of application Ser. No. 114,618 filed Oct. 29, 1987, now U.S. Pat. No. 5,243,038, which is a continuation-in-part of application Ser. No. 927,258, filed Nov. 4, 1986, now abandoned and claims priority to PCT 89/05016, filed Nov. 7, 1989.

TECHNICAL FIELD

The field of this invention is thermoplastics incorporating thermostable polypeptides.

BACKGROUND

The immobilization of functional polypeptide provides an enormously broad range of applications from medical diagnostics, medical implants, chemical separations, chemical sensors, cultureware, etc. Because of their relatively low reactivity and expense, plastics are the most common solid substrates for protein immobilization. Heat is often used in the fabrication of useful articles from thermoplastic resins and elastomers as well as thermosetting resins and elastomers. Typically the heating and extrusion/molding process requires temperatures in the 100°–400° C. range and often much higher.

Most polypeptides are irreversibly denatured and loose their functional properties at temperatures above about 50°–60° C. The exceptions are polypeptides of a few thermophilic bacteria surviving the environs of hot springs and undersea thermal vents which have recently been shown to have heat stabilities up to 100° C. To accommodate the thermal lability of polypeptide function, immobilization with plastic is accomplished by attaching a selected polypeptide to a pre-formed plastic surface either covalently, usually by chemical activation of the substrate surface, or non-covalently, usually called adsorption.

The vast majority of plastics have hydrophobic surfaces. For many applications such as cell culture and immunodiagnostics, it is critical to have a hydrophilic surface that aqueous fluids will wet. Current treatments commercially employed include plasma treatment to cause the formation of ionizable chemical groups on the surface, oxidation under conditions of irradiation, or by deposition of surfactants on the surface.

Accordingly, there are a number of deficiencies with current polypeptide immobilization methods and compositions. Solvent, vapor or powder deposition are labor, time and material intensive. Surface coatings are subject to mechanical wear and erosion, chemical modification or degradation, and removal by the action of solvents. Some articles, such as bottles, are difficult to surface coat. And, especially in the case of cultureware, post-manufacture sterilization steps are often required.

Relevant Literature

Wood and Gadow (1983) J Clin Chem Clin Biochem 21, 789–797 review immobilization of proteins on solids; Ponnuswamy et al (1982) Int J Biol Macromol 4, 186–190; Dale et al and Wampler et al (1992) ACS Symp Ser 498 (Biocatal Extreme Temp), 136–152 and 153–173; Finkelstein and Reva (1991) Nature 351, 497–499; Goodenough and Jenkins (1991) Biochem Soc Trans 19, 655–662; Wozniak et al (1990) Crystallogr Model Methods Mol Des, Ed. Bugg and Ealick, New York, N.Y.; Mathews et al (1987) Proc. Natl. Acad. Sci. 84, 6663–6667 discuss protein compositional parameters relating to thermal stability; Santoro et al (1992) Biochemistry 31, 5278–5283; Lucy and Lee (1987) Biochemistry 26, 7813–7819; MacLeod et al (1984) Res Discl 244, 380 describe agents which affect the thermal stability of proteins.

SUMMARY OF THE INVENTION

The present invention relates to the finding that certain polypeptides can maintain functional integrity through exposure to plastic thermomolding. Accordingly, thermoplastics containing a variety of functional thermostable polypeptides and methods of making such polypeptide containing thermoplastics are provided. The polypeptides are exposed to the heating and molding/extrusion/casting process and are hence present on the formed plastic surface and at a depth below the plastic surface. The polypeptides contained in the disclosed compositions retain functional properties through the heating and molding/extrusion/casting processes. Preferred thermostable polypeptides used in the disclosed compositions include silk-like protein polymers, particularly ProNectin®F. The disclosed methods and compositions find use in many applications where plastics containing functional polypeptides are desired, in particular, cell cultureware.

BRIEF DESCRIPTION OF THE DRAWINGS

FIG. 1. HT 1080 Cell Attachment/SDS Development.

FIG. 2A-1 & FIG. 2A-2. PC12 Neurite Outgrowth Evaluation of SLPL3.0 Polymer.

FIG. 2B-1 & FIG. 2B-2. PC12 Neurite Outgrowth Evaluation of SLPL3.0 Polymer.

FIG. 2C-1 & FIG. 2C-2. PC12 Neurite Outgrowth Evaluation of SLPL3.0 Polymer.

FIG. 2D-1 & FIG. 2D-2. PC12 Neurite Outgrowth Evaluation of SLPL3.0 Polymer.

DESCRIPTION OF SPECIFIC EMBODIMENTS

Figures 1, 2A:
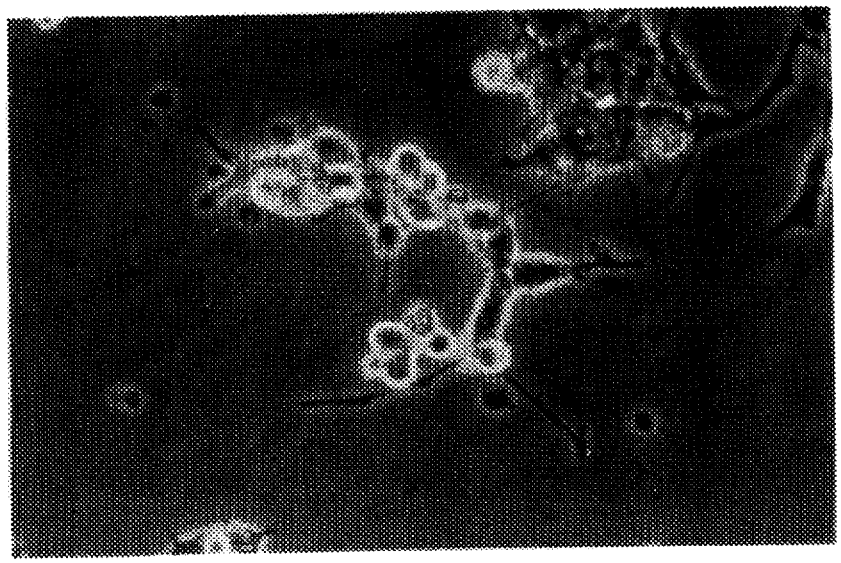

The invention provides methods and compositions relating to thermoplastics containing functional thermostable polypeptides. These compositions present numerous advantages over conventionally coated plastics: increased durability of the surface activation to mechanical wear and erosion or the action of solvents, increased resistance to chemical modification or degradation, lower costs of production, broader range of articles for manufacture, etc.

The thermoplastics of the invention are broadly defined to encompass a wide variety of chemical compositions. By "plastic" is meant a polymeric material, preferably organic, of large molecular weight, usually between $10^3$ and $10^6$ MW, which can be shaped by flow. In addition to the base resin, formulations of thermoplastic, including thermosetting polymers, for use in thermomolding applications may include a variety of additives such as stabilizers, accelerators, retardants, antimicrobials, lubricants, fillers, plasticizers, pigments, etc. However, in certain embodiments, some additives interfere with the presentation or function of polypeptides at the surface. For example, as shown below, zinc stearate can exhibit a blooming effect whereby surface polypeptide is masked by migrating small molecular weight compounds. Similarly, the compatibility of any selected additive with the methods and compositions disclosed herein is readily determined.

Preferred plastics are amenable to injection molding (they are melt processable at less than about 300° C. and have Tg's of less than about 200° C.), and are least reactive toward the selected thermostable polypeptide, in particular, under injection molding conditions. Plastics with a potential of engaging in amidation or transamidation reactions, such as polyamides or polyesters are less desirable. Most preferred plastics include polystyrene, polypropylene, polyethylene and polyvinyl chloride. Other useful plastics include polyvinylidene fluoride, polyvinylidene chloride, acrylonitrile butadiene styrene (ABS), styrene acrylonitrile (SAN), and polyacrylonitrile (PAN). Plastics which find use but also entail chemical reactivity toward some polypeptide groups include both aromatic and aliphatic polyamides and polyimides, polyacrylates, polymethacrylate esters, polydioxanone, polyanhydrides, and polyesters such as polycarbonate, polybutylene terphthalate, polyethylene terphthalate, polyglycolic acid and polylactic acid and PLGA copolymers, polyhydroxybutyrate (PHB), polyurethanes, and homopolymers and copolymers of polyvinyl alcohol esters such as polyvinyl acetate and ethylene vinyl acetate. Plastics may also include rubbers such as polysiloxanes, polybutadienes, and neoprenes. However, any plastic capable of thermal extrusion/casting/molding may find use herein.

As numerous applications of the disclosed compositions involve contact with viable biological cells or tissue, biocompatible plastics are especially preferred. Biocompatible plastics are typically non-toxic, biochemically inert, and nonproductive of undesired immune responses when used in vivo. Exemplary biocompatible plastics include polycaprolactone, polycarbonate, polydimethylsiloxane (silicone rubber), polydioxanone, polyether urethane, polyethylene and polyethylene terphthalate, polyglycolic acid and polylactic acid and PLGA copolymers, polyhydroxyethyl methacrylate (HEMA), polymethylmethacrylate (acrylic), and polyvinyl chloride (PVC). Also useful are biodegradable plastics, preferably plastics that degrade under physiological conditions, including polycaprolactone, polydioxanone, polyglycolic acid and polylactic acid and PLGA copolymers, and polyanhydrides. Such plastics are especially useful in diagnostics, therapeutics, and environmental monitoring where time-release of the contained polypeptides or where subsequent removal of the plastic is inconvenient.

The plastics which are mixed with a thermostable polypeptide according to the present invention may be obtained in any convenient form and are generally commercially available or readily obtained by those of ordinary skill in the art. Generally, a polymerized form is preferred; though, where the polymerization conditions are compatible with the preservation of polypeptide functional integrity, monomers may be used. The compatibility of the polypeptide with the polymerization depends in large part on the reactivity of the particular amino acid composition of the selected protein in the polymerization reaction. For example, vinyl polymerization finds some use while condensation polymerization of polyesters and polyamides is less useful.

The thermostable polypeptides are interdispersed or present on the surface of the plastics as well as being contained within the plastics of the invention. By interdispersed is meant that at least some of the polypeptide is found beneath the surface of the plastic. Prior art plastics have been surface coated with polypeptide from solution or dispersion in liquids or in powder form. By incorporating the thermostable polypeptide before or during the thermomolding process rather than as a post-molding coating step, the present invention provides subsurface polypeptide as opposed to solely a surface coating layer on the plastic. Accordingly, the disclosed materials do not have a clearly defined polypeptide-plastic interface. In a preferred embodiment, the thermostable polypeptide is present throughout most of the volume of the thermomolded plastic object. The thermostable polypeptide is present in the range of about 1–10,000 ppm; generally, at less than 2,000 ppm, preferably less than 500 ppm, more preferably less than 100 ppm. Polypeptide is usually detectable at concentrations greater than 1 ppm, preferably greater than about 10 ppm, at a depth of 0.1 um, preferably 0.1 um, and more preferably at least about 1 um below the surface of the plastic.

By functional thermostable polypeptide is meant a protein, polypeptide, or peptide that at least partially retains the native protein, polypeptide or peptide's structure (primary, secondary or tertiary) and retains one or more specific functions of the native polypeptide after exposure to the thermal molding/extrusion/casting conditions described herein. Exemplary retained specific functions include catalytic or enzymatic activity, binding specificity, specific covalent, ionic, or non-covalent interactions with the environment for example, chemical conjugation with various reagents, and to a less preferred extent, defined wettability, ionic conductance, etc. By binding specificity is meant a molecular spatial orientation specifically recognizable by, for example, a protein receptor. Examples include cellular ligands (an epitope to which cell surface receptors bind), immunological epitopes (an epitope to which an antibody binds), sugar moieties (an epitope to which a lectin may bind), peptide-specific epitopes (an epitope to which a peptide—usually a synthetic peptide of 3–60 residues screened for component-specific binding from peptide libraries or denovo design—bind), etc.

Functional thermostable polypeptides are readily identified by function assays of processed plastic containing the polypeptide, commonly cell culture or protein or ligand binding assays, including those used to assess the function of polypeptides immobilized on surfaces using previous methods in the art, although many other assays may be employed, depending upon the function, which will be readily recognized by those skilled in the art. For example, catalytic activity, binding specificity, physical chemical properties, etc. are all readily tested by conventional immunoassays, spectroscopy, microscopy, etc. Candidate polypeptides for the above functional assays are selected by the potential market of their intended application and predicted functional thermostability. Indications of functional thermostability include resistance to decomposition or irreversible denaturation so as to lose their desired function under the plastic processing conditions; inclusion of relatively few amino acids susceptible to high temperature chemical modification or cleavage such as lysine and aspartic acid; inclusion of relatively high proportions of amino acids known to be associated with thermally stable polypeptides such as arginine, alanine, threonine, asparagine, isoleucine, or glutamic acid; structures with a high degree of intrachain bonding such as hydrogen bonds or covalent cross-links; hydrogen bonded antiparallel beta sheets with a high accessible surface area; and activity or functionality contained in a single chemically contiguous protein or peptide chain.

The polypeptides are typically of large molecular weight, usually more than about 6 kD, preferably more than 25 kD, more preferably more than 50 kD. However, polypeptides of at least 3, preferably at least about 6, more preferably at least about 12, most preferably at least about 24 amino acids in length may also be employed. Preferred thermostable polypeptides include structural proteins such as elastin-, collagen-, keratin-, and silk-type proteins, preferably, proteins derived from thermophilic bacteria such as *Sulfolobus solfataricus* and *Thermus aquaticus* (enzymes such as proteases, DNA polymerases, lipases, and metabolic enzymes are especially useful), and more preferably, synthetic protein polymers, particularly proteins designed with silk-like protein, SLP blocks (SLPF or FCB-SLPIII (fibronectin), SLPL (laminin), SLPC (cystine), SLP3, SLP4, and SELPs (elastin) as described in U.S. patent application Ser. Nos. 609,716 and 114,618, and peptides designed with SLP blocks (peptide 92.7: KKMGAGAGSGAGAGSGAAVTGRGDSPASAAGYGA-GAGSGAGAGS), (SEQ ID NO:01) where ProNectin®F (PnF, SLPF or FCB-SLPIII) is most preferred. The polypeptides may be natural, chemically synthesized, or recombinant proteins, including modified forms such as mutants and fusion products, and also including modifications against thermally induced degradation or denaturation, for example, pegylation.

The genes of the subject invention comprise multimers of DNA sequences encoding the same amino acid sequence unit, where two or more different multimers encoding different amino acid units may be joined together to form a block copolymer. The individual units will have from 3–30 amino acids (9–90 nt), more usually 3 or 4 to 25 amino acids (9–75 nt), particularly 3 or 4 to 15 amino acids (9–45 nt), or particularly 3 or 4 to 9 amino acids (9–27 nt), usually having the same amino acid appearing at least twice in the same unit, generally separated by at least one amino acid. The units of the multimer coding for the same amino acid sequence may involve two or more nucleotide sequences, relying on the codon redundancy to achieve the same amino acid sequence.

Peptide polymers having intervening sequences may provide for chemically active amino acids for chemical crosslink sites, which may serve to covalently attach functional peptides, synthetic or natural polymers or proteins, non-amino acid molecules, and the like. The intervening sequence may be a naturally occurring sequence or a modified naturally occurring sequence. Naturally occurring sequences may be derived from a wide variety of sources with a variety of functions. Such sequences may be a cellular growth inhibitor sequence e.g., from Tenascin; cell growth promoting attachment factors, e.g., from fibronectin, RGD-, -REDV-; laminin B1-YIGSR-; bacterial adhesive-SLF-, -ALF-; growth hormones and insulin; inclusion sequences (GAGC and GCCV, which provide systems for attachment and crosslinking; VSPD, VCDP and DPGK, which provide an underlining structure).

By thermomolding is meant that the plastic is exposed to heat in the fabrication process. Generally, heat is used to melt the plastic for molding, and, in the present invention, for distributing polypeptide beneath the surface of the plastic. Thermomolding refers to any method of heating and forming the plastic and includes extrusion, injection molding, thermoforming, thermosetting, compression molding, etc. Extrusion includes die, cast film, sheet, profile and wire processes. Injection molding is preferred for most articles, especially cultureware, and includes structural foam, blow molding (useful for producing roller bottles), and rotational molding. Less preferred embodiments include reaction injection molding because of potential cross-reactivity with the polypeptide.

Thermomolding is generally performed according to conventional methods. This molding step is usually performed at temperatures in excess of 60° C., preferably in excess of 100° C. and more preferably in excess of 140° C.; though temperatures in excess of 200° C. and 300° C. also find use herein. The manufacturing temperature is determined by the character of the plastic resin as well as the thermostability of the polypeptide. Thermal stability boundaries are readily determined using the methodologies described below. A variety of methods may be employed to enhance the thermal stability of the polypeptides under the thermomolding conditions, such as the addition of organic acids, divalent cations, zwitterions, or saccharides, and decreases in the moisture content of the mixture of polypeptide and plastic prior to thermomolding. As exemplified below, the IKVAV presenting domain of SLPL3.0 which was inserted into SLP3 contains a lysine, which is less reactive when protonated. Residual formic acid was left in the polystyrene powder coated with SLPL3.0 and enhanced performance was observed after thermomolding compared to the untreated control. Similarly, $Ca^{2+}$ and glycine were shown to confer additional resistance to thermal degradation in the case of polystyrene powder coated with PnF.

The polypeptide may be added at a variety of stages of the manufacturing process so long as heat is applied during or after the addition of the protein. Thus for example, polypeptide (in solution or dry) may be mixed with commercial resin pellets before heating and extrusion, with a melt before, in, or after the final metering of the extruder, etc. Dispersing agents known to those skilled in the art may be used to enhance mixing of polypeptides into the plastics under thermomolding conditions. The polypeptide may be added before extrusion and the extruded ribbon reheated while being compressed in to the final article. Alternatively, the polypeptide can be applied to the surface of the extruded ribbon and then compression molded to form the final article. For instance, a film can be coated and then heated in a mold to form a microliter plate.

The thermomolded polypeptide-enriched plastics may take a wide variety of forms depending on the intended application. Preferred forms include sheets, membranes, beads, fibers, hollow fibers, tubes and formed vessels. Preferred vessels include tissue culture matrices such as petri dishes, culture flasks, roller bottles and microliter-type plates. The plastics may be solid, porous, or semiporous and may be made bio- or environmentally degradable by techniques described herein or otherwise known to those skilled in the relevant art.

The polypeptide-enriched thermoplastics of the present invention find a wide variety of uses, especially in the chemical, biotechnology, and health care industries. The materials find use, for example, in separation techniques such as chromatographic or filtration matrices; in therapeutic techniques such as controlled drug delivery (e.g. transdermal skin patches and osmotic pumps), sutures, catheters, etc.; in diagnostic techniques; and in tissue culture matrices.

EXAMPLES

Construction of SLP-F9

Two oligonucleotide strands were synthesized and purified as described in the Methods section of the U.S. application Ser. No. 07/609,716.

| | | | | | | (PstI) | SnaBI | | | | | (PstI) | | | | (SEQ ID NO:2) | i) 5'-     CGCTAGTTCTGCCACGTCCGGTATGTTTCGAAAAAGCTGCA     -3' ii) 3'-     ACGTGCGATGCATCAAGACGGTGCAGGCCATACAAAGCTTTTTCG-5'     (SEQ ID NO:3)

These oligonucleotide strands were annealed and ligated with plasmid pSY1304 which had been digested with PstI REN.

The product of this ligation reaction was transformed into *E. coli* strain HB101. Plasmid DNA from transformants was purified and digested with BanI; clones containing inserts of the correct size were digested with BsaAI REN to determine the restriction pattern. Plasmid DNA from correct clones was sequenced. Plasmid pPT0272 (shown in Table 1) contained the desired SLP-F9 monomer sequence.

TABLE 1

| GGT | GCC | GGC | AGC | GGT | GCA | GGA | GCC | GGT | TCT | GGA | GCT | GGC | GCG | GGC | TCT | GGC | GCG | GGC |
|---|---|---|---|---|---|---|---|---|---|---|---|---|---|---|---|---|---|---|
| G | A | G | S | G | A | G | A | G | S | G | A | G | A | G | S | G | A | G |
| GCA | GGA | TCC | GGC | GCA | GGC | GCT | GGT | TCT | GGC | GCA | GGG | GCA | GGC | TCT | GGC | GCA | GGA | GCG |
| A | G | S | G | A | G | A | G | S | G | A | G | A | G | S | G | A | G | A |
| GGG | TCT | GGA | GCT | GCA | CGC | TAC | GTA | GTT | CTG | CCA | CGT | CCG | GTA | TGT | TTC | GAA | AAA | GCT |
| G | S | G | A | A | R | Y | V | V | L | P | R | P | V | C | F | E | K | A |
| GCA | GGC | TAT | GGA | GCT | GGC | GCT | GGC | TCA | GGT | GCT | GGA | GCA | GGA | AGC | GGA | GCG | (SEQ ID NO:4) | |
| A | G | Y | G | A | G | A | G | S | G | A | G | A | G | S | G | A | (SEQ ID NO:5) | |

Plasmid DNA from pPT0272 was digested with BanI REN and the digestion fragments were separated by agarose gel electrophoresis. The SLP-F9 gene fragment, 222 bp, was excised and purified by NACS column (see Example 1 of U.S. application Ser. No. 07/609,716). The purified fragment was ligated with plasmid pSY1262 which had been digested with REN BanI. The product of this ligation reaction was transformed into *E. coli* strain HB101. Transformants were selected for resistance to kanamycin. Plasmid DNA from individual transformants was purified and analyzed for increased size due to SLP-F9 multiple DNA insertion. Several clones were obtained ranging in size from 1 kbp to 4 kbp. One clone pPT0275, with an insert of approximately 2.7 kbp was chosen for expression and protein analysis.

SLP-F9 Expression

An overnight culture which had been grown at 30° C. was used to inoculate 50 ml of media contained in a 250 ml flask. Kanamycin was added at a final concentration of 50 µg per ml and the culture was incubated with agitation (200 rpm) at 30° C. When the culture reached an $OD_{600}$ of 0.8, 40 ml were transferred to a new flash prewarmed at 42° C. and incubated at the same temperature for approximately 2 hours. The cultures (30° and 42°) were chilled on ice and $OD_{600}$ was taken. Cells were collected by centrifugation divided in 1.0 $OD_{600}$ aliquot and used to perform dot blot and western analysis using SLP antibodies. For purification and amino acids analysis larger cultures were used.

MDPVVLQRRDWENPGVTQLNRLAAHPPFASDPMGAGS (GAGAGS)$_6$
[GAA RYVVLPRPVFEKAAGY (GAGAGS)$_9$]$_{11}$
GAARYVVLPRPVCFEKAAGY (GAGAGS)$_2$ GAGAMDPGRYQLSAGRYHYQLVWCQK (SEQ ID NO:06)

Construction of SLP-L3.0

An additional two oligonucleotide strands were synthesized as described in the Methods section of U.S. application Ser. No. 07/609,716.

| | | (PstI) | | ClaI | | (PstI) | (SEQ ID NO:07) | iii) 5'-     CCGGGTGCATCGATCAAAGTAGCTGTTAGCGCCGGACCGTCTGCA-3' iv) 3'-AGCTGGCCCACGTAGCTAGTTTCATCGACAATCGCGGCCTGGCAG     5'     (SEQ ID NO:08)

These oligonucleotide strands were annealed and ligated with plasmid pSY1304 which had been digested with PstI REN.

The product of this ligation reaction was transformed into *E. coli* strain HB101. Plasmid DNA from transformants was purified and digested with BanI; clones containing inserts of the correct size were digested with StuI and ClaI RENs to determine the restriction pattern. Plasmid DNA from correct clones was sequenced. Plasmid pPT0271 (shown in Table 2) contained the desired SLP-L3.0 monomer sequence.

4.5M $LiClO_4$ and diluted in phosphate buffered saline (PBS) to concentrations ranging from 100 to 0.14 µg/ml. 0.1 ml of the diluted polymer solution was dispensed to individual wells of a tissue culture polystyrene multi-well dish. The solution was left in contact with the surface of the dish for 2 hours then the dish was rinsed with PBS several times and incubated with freshly harvested HT1080 cells in serum-free medium. After one hour, unattached cells were removed by rinsing in PBS and attached cells were fixed and stained with a blue dye. The stained cells were quantified by solubilizing

TABLE 2

| GGT | GCC | GGC | AGC | GGT | GCA | GGA | GCC | GGT | TCT | GGA | GCT | GGC | GCG | GGC | TCT | GGC | GCG | GGC | |
|---|---|---|---|---|---|---|---|---|---|---|---|---|---|---|---|---|---|---|---|
| G | A | G | S | G | A | G | A | G | S | G | A | G | A | G | S | G | A | G | |
| GCA | GGA | TCC | GGC | GCA | GGC | GCT | GGT | TCT | GGC | GCA | GGG | GCA | GCC | TCT | GGC | GCA | GGA | GCG | |
| A | G | S | G | A | G | A | G | S | G | A | G | A | G | S | G | A | G | A | |
| GGG | TCT | GGA | GCT | GCA | CCG | GGT | GCA | TCG | ATC | AAA | GTA | GCT | GTT | AGC | GCC | GGA | CCG | TCT | |
| G | S | G | A | A | P | G | A | S | I | K | V | A | V | S | A | G | P | S | |
| GCA | GGC | TAT | GGA | GCT | GGC | GCT | GGC | TCA | GGT | GCT | GGA | GCA | GGA | AGC | GGA | GCG | GGT | GCC | (SEQ ID NO:09) |
| A | G | Y | G | A | G | A | G | S | G | A | G | A | G | S | G | A | G | A | SEQ ID NO:10) |

Plasmid DNA from pPT0272 was digested with BanI REN and the digestion fragments were separated by agarose gel electrophoresis. The SLP-L3.0 gene fragment, 222 bp, was excised and purified by NACS column (see Example 1 of U.S. application Ser. No. 07/609,716). The purified fragment was ligated with plasmid pSY1262 which had been digested with REN BanI. The product of ligation reaction was transformed into *E. coli* strain HB101. Transformants were selected for resistance to kanamycin. Plasmid DNA from individual transformants was purified and analyzed for increased size due to SLP-L3.0 multiple DNA insertion. Several clones were obtained ranging in size from 1 kbp to 4 kbp. One clone pPT0278, with an insert of approximately 2.9 kbp was chosen for expression and protein analysis.

SLP-L3.0 Expression

An overnight culture which had been grown at 30° C. was used in inoculate 50 ml of media contained in a 250 ml flask. Kanamycin was added at a final concentration of 50 µg per ml and the culture was incubated with agitation (200 rpm) at 30° C. When the. culture reached an $OD_{600}$ of 0.8, 40 ml were transferred to a new flask prewarmed at 42° C. and incubated at the same temperature for approximately 2 hours. The cultures (30° and 42°) were chilled on ice and $OD_{600}$ was taken. Cells were collected by centrifugation divided in 1.0 $OD_{600}$ aliquot and used to perform dot blot and western analysis using SLP antibodies. For purification and amino acids analysis larger cultures were used.

the dye and determining its solution absorbance by spectrometry at a wavelength of 595 nm.

The attachment experiment was run in parallel with wells coated with fibronectin and a synthetic peptide of the sequence RKQAASIKVAVS (SEQ ID NO:12). FIG. 1 shows a titration curve for cell attachment as a function of coating concentration. The results indicate that SLP-L3.0 (shown as LAM 3.0) promotes the attachment of HT1080 cells to tissue culture polystyrene coated with the polymer in a dose dependent manner. Maximum activity is observed at the greatest coating concentration used in this experiment, 100 µg/ml. Although the activity drops with coating concentration, cell attachment is observed greater than background even at the lowest concentration, 0.14 µg/ml. The polymer has significantly greater activity than the laminin peptide at concentrations of 74 µg/ml or less. Considering the difference in molecular weight between the polymer and the synthetic peptide, the polymer has 32 times greater activity than the peptide on the basis of number of active sequences. The polymer compares favorably with the attachment activity of fibronectin, even though different binding receptors would be utilized in each case.

In order to evaluate the polymer's ability to stimulate neurite outgrowth, PC12 cells were grown on plastic dishes coated with polylysine, collagen type I, fibronectin, the peptide RKQAASIKVAVS (SEQ ID NO:12), SLP-L3.0, and laminin. The cells were stimulated with nerve growth factor

---

MDPVVLQRRDWENPGVTQLNRLAAHPPFASDPMGAGS (GAGAGS)₆
[GAA PGASIKVAVSAGPSAGY (GAGAGS)₉]₁₂
GAAPGASIKVAVSAGPSAGY (GAGAGS)₂ GAGAMDPGRYQLSAGRYHYQLVWCQK (SEQ ID NO:11)

---

Activity of SLP-L3.0

SLP-L3.0 was purified from *E. coli* strain pPT0278 using standard extraction and protein separation techniques. Purity of the final product was determined by amino acid compositional analysis and microchemical elemental analysis to be 94.6% by weight.

Figures 2, 2A:
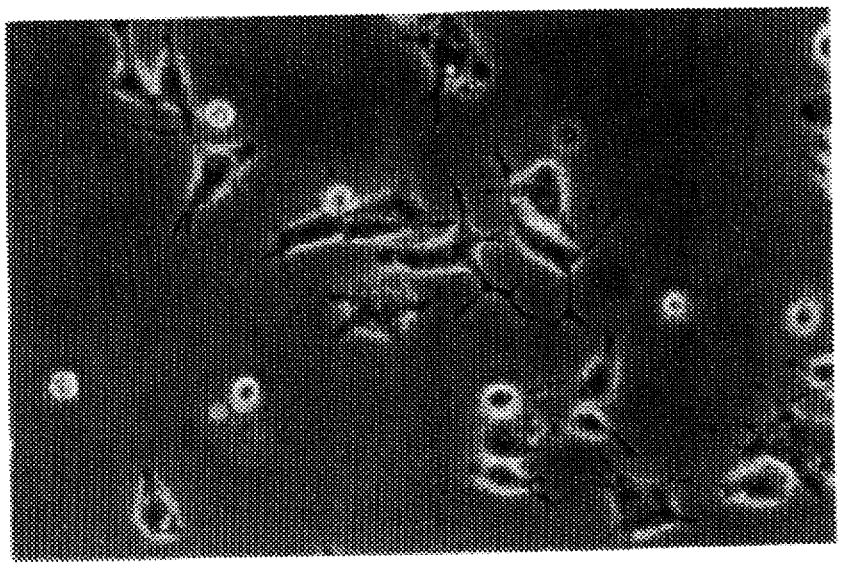
Figures 1, 2B:
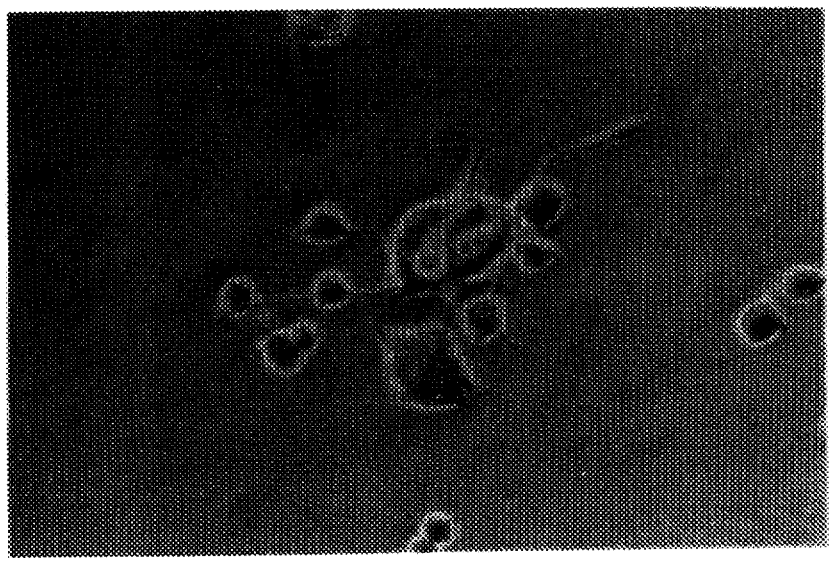
Figures 2, 2B:
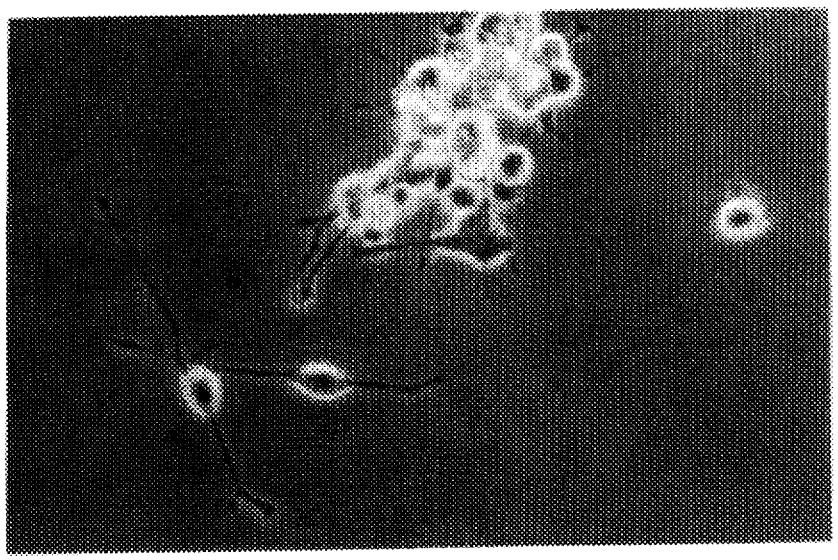
Figures 1, 2C:
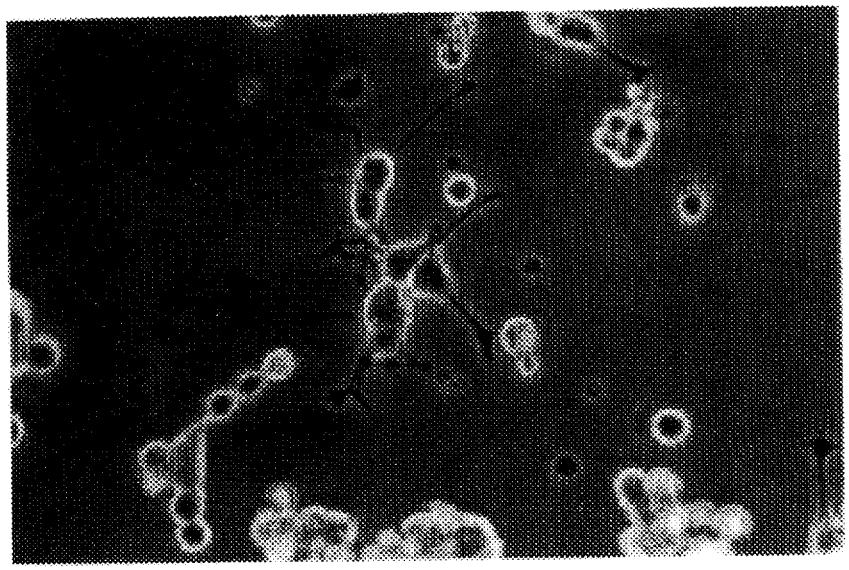
Figures 2, 2C:
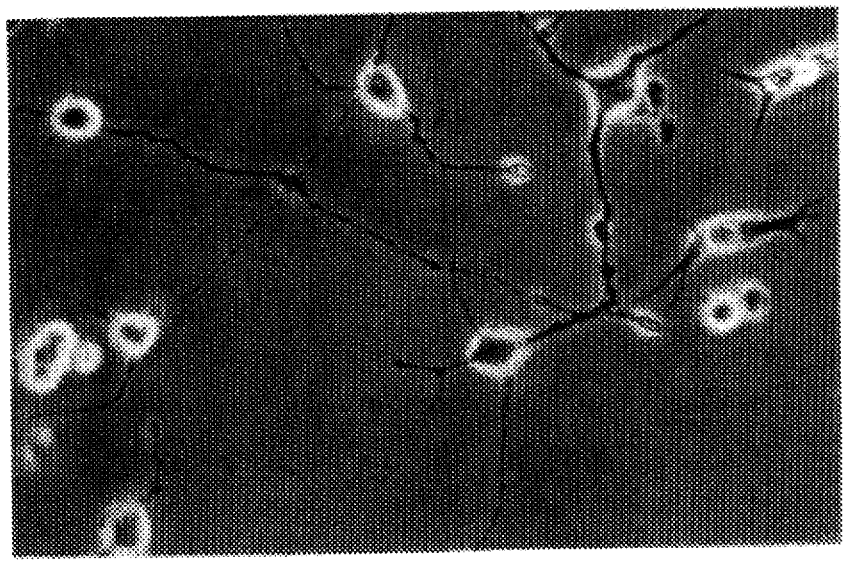
Figures 1, 2D:
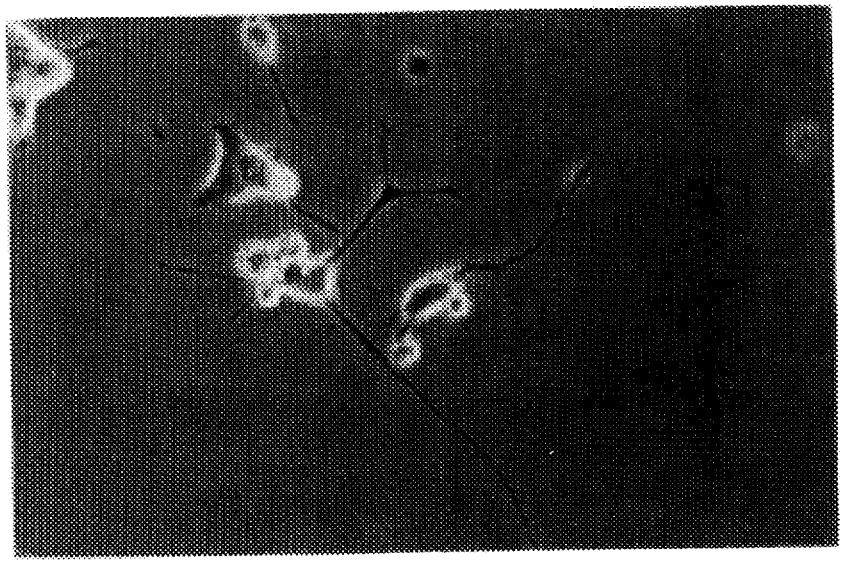
Figures 2, 2D:
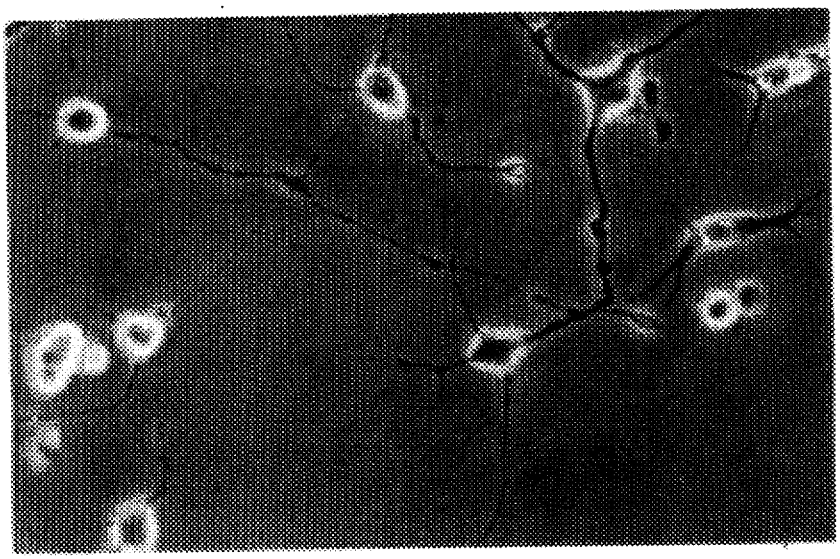

SLP-L3.0 was evaluated for its ability to promote the attachment of a fibrosarcoma cell line, HT1080, commonly used for attachment assays on collagen, fibronectin and laminin. The purified product was dissolved in a solution of to undergo neural differentiation. The number and lengths of neural cell processes that extended from these cells were observed and photographed. FIG. 2 shows the degree of neural differentiation observed for the PC12 cells grown on the various coatings for 1 day. SLP-L3.0 did promote neural outgrowth of PC12 cells to a significantly greater degree than uncoated dishes. The activity of SLP-L3.0 was greater than all of the substrates except laminin.

Extrusion of polystyrene coated with ProNectin®F

Crystalline polystyrene (PS) pellets (454 grams) were washed with isopropyl alcohol (500 ml per wash) three times to remove surface contaminants and then air dried. The pellets were rinsed in 800 mls of phosphate buffered saline (PBS). A solution containing 200 mg of ProNectin®F (SLPF batch RX4, Protein Polymer Technologies, Inc.) dissolved in 20 mls of 4.5 Molar lithium perchlorate was diluted by adding 780 ml of PBS to yield a final ProNectin®F concentration of 0.25 mg/ml. The solution was then added to the pellets and stirred gently overnight for maximum adsorption of the ProNectin®F on the polystyrene surface. The pellets were then rinsed three times with deionized water then air dried.

The amount of ProNectin®F adsorbed to the surface of the polystyrene pellets was measured by amino acid analysis. Coated pellets (253 mg) were placed in a sealed glass hydrolysis vial containing 100 µl of 0.1N HCl and flushed with nitrogen gas. The vial was incubated at 100° C. for 24 hrs. The liquid contained in the vial was removed and the pellets rinsed with 150 µl of 0.1N HCl The hydrolysis solution and the rinse were combined in a tube and dried under vacuum. The amino acid residues contained in the tube were derivatized by addition of isophenylthiocyanate according to standard protocols. The derivatized amino acids were separated by HPLC reverse phase chromatography, detected spectroscopically and quantified based on their adsorption as compared to known standards. The pellet hydrolysis was shown to contain 6.6 µg of amino acids per 253 mg of coated polystyrene or 26.1 µg of amino acids/g polystyrene. The dimensions of an average pellet were measured and the surface area was calculated to be approximately 0.3 $cm^2$/13 mg or 23 $cm^2$/g. Therefore, the coated pellets contained on average 26.1 µg of amino acids/23 $cm^2$ of polystyrene or 1.1 ug/$cm^2$. That ProNectin®F was the only source of the amino acids on the coated pellets is evidenced by the fact that the amino acid content of the polystyrene hydrolysate closely matched the amino acid content of the ProNectin®F batch used in the coating. Accordingly, this procedure deposited approximately 1.1 µg of ProNectin®F per $cm^2$ of polystyrene surface area.

The dried ProNectin®F-coated pellets were fed into a heated single screw extruder fitted with a 2"×⅛" ribbon die. Temperature was controlled in the extruder barrel to maintain the polystyrene melt temperature at 390 Fahrenheit. A first extrusion was made on a moving belt to produce a continuous ribbon. The ribbon was allowed to cool and then cut into 2"×2" pieces. A second extrusion was conducted whereby the continuous ribbon was passed to a Carver press fitted with heated platens and compressed to ¹⁄₁₆" thickness. The cooled ribbon was then cut into 2"×2" pieces.

Cut pieces of both the raw extruded and compression molded polystyrene ribbon were placed in 100 mm diameter polystyrene petri dishes. Delbecco's Modified Eagles Medium (DMEM) (25 ml) was added to the dishes to cover the cut pieces. Medium was also placed in empty polystyrene petri dishes to serve as negative controls. A suspension (25 ml) of viable African Green Monkey Kidney (VERO) cells at $4\times10^5$ cells per ml were pipetted into all petri dishes and allowed to settle on the cut pieces or empty dish bottom. The petri dishes were then incubated for 1.5 hrs at 37 C in a 5% $CO_2$ atmosphere to allow cell attachment. The cut pieces and empty dishes were washed twice with PBS to remove unattached cells and then 3% formaldehyde solution was added to fix attached cells by standing at room temperature for 5 min. The fixed cells were stained by adding 0.1% amido black in 40% methanol and 10% acetic acid solution. After 10 min staining the cut pieces and empty dishes were destained in 90% methanol, 8% acetic acid, 2% water. Attached cells were observed microscopically and photographed.

Both the raw extruded and compression molded polystyrene pieces showed considerable darkening on their surface indicating adsorption of the amido black stain by attached cells, whereas the empty polystyrene dishes showed no color development on the dish bottom indicating the lack of attached cells. Microscopic observation confirmed that the raw extruded and compression molded polystyrene surfaces were covered with attached cells, whereas the empty polystyrene dishes showed no color development on the dish bottom indicating the lack of attached cells. Microscopic observation confirmed that the raw extruded and compression molded polystyrene surfaces were covered with attached cells, whereas the empty polystyrene dishes lacked cell attachment.

The presence of attached cells on the extruded polystyrene and lack of attached cells on the empty dishes substantiates that the functionality of ProNectin®F as a cell attachment ligand was maintained through the extrusion process.

Non-Washed Powdered Polystyrene

A mixture of solid dry ice for cooling and polystyrene pellets without added zinc stearate, lubricants, or waxes (Amoco IR3-C0) was ground to a powder without added suspending liquid using a standard laboratory Waring blender. The polystyrene powders were sized using American Standard stainless steel sieves. Polystyrene powder of >100 mesh was taken for these experiments. No attempt was made to wash the polystyrene after the grinding operation. ProNectin®F (4 mg) was dissolved in 30 ml of 85% formic acid, slurried with 10 g of the sieved polystyrene powder, and concentrated to dryness on the rotary evaporator using bath temperatures of less than 60° C. Several sample films from each lot of powder were compression molded from 250 mg of coated polystyrene powder between 304 stainless steel plattens using a Carver press with plattens heated electrically to 150° C. and a maximum force of 1500 Kg for 5–10 seconds. Disks of 7 mm diameter were punched out of the films and were placed in individual wells of a 96 well tissue culture plate. The cell attachment assay was conducted as described below. Film samples were assayed in quadruplicate. The goal of this set of experiments was to explore methods of washing the films after they were installed into the tissue culture plate. Combinations of isopropanol, 1 mmolar aqueous EDTA, and 1% (w/v) Triton X-100 were used for these washes. A few disks in two lanes showed positive cell attachment signals. No obvious correlation with processing protocols could be established from these experiments.

Attachment Assay Using VERO Cells

The silicone grease "adhesive" used to affix compression molded test disks to the tissue culture plates was prepared by diluting Dow Corning High Vacuum Grease with cyclohexane to a final concentration of 25% w/v, centrifuging to compact the silica filler, and retaining the supernatant. To each well of a 96-well tissue culture plate which is to receive a test disk was added 25 µl of the silicone adhesive solution. The plate was then dried overnight in a vacuum oven at 40° C. In all operations, best results were obtained when all wash and aspiration steps were performed using a Biotek 403H automated plate washer with settings: dispense height=10; plate height=100; dispense volume=200 µl; and number of washes=2.

One lane of the plate as a positive control, was solution coated with ProNectin®F. A stock solution of ProNectin®F (1 mg/ml) was prepared in 4.5 Molar aqueous lithium perchlorate. This stock solution (10 μl) was diluted into 10 ml of 1× calcium-magnesium free phosphate buffered saline (cmf PBS) to yield a coating solution with a final concentration of 1 μg/ml. Coating solution (100 μl) was added to each well which is to serve as a positive control and incubated at room ambient temperature for 1.5 hours.

While the positive control lane was being solution coating with ProNectin®F, the 7 mm diameter test disks were placed into 5 dram vials and washed 3 times with 5 ml of 1× cmf PBS. The test disks were then placed into each well and gently pressed into the silicone grease which had been layered on the bottom of the well. After mounting the test disks into the plate, they were washed twice with 200 μl of 1× cmf PBS. At this time, the background absorbances were read using a Titertek Plate Reader at 595 nm. Blocking solution (2 mg of bovine serum albumin per milliliter of cmf PBS), 100 μl, was added to each well and incubated for 2 hours at room ambient temperature and one hour at 37° C. The blocking solution was aspirated and the plate rinsed once with 1× cmf PBS.

VERO cells, $2 \times 10^5$ cells from a suspension prepared at $2 \times 10^6$ cells/ml, were added to each well using DME culture media without fetal bovine serum and the plate incubated for 1 hour in 5% carbon dioxide at 37° C. The media containing the cells was aspirated and the plate rinsed twice with 200 μl 1× cmf PBS. Fixative solution (3.7% formaldehyde in 1×cmf PBS), 100 μl, was added to each well and incubated for 5–10 minutes at room ambient temperature. The fixative solution was aspirated. Staining solution (0.1% amido black in 40% methanol-10% acetic acid), 100 μl, was added, and the plate was incubated for 30–60 minutes at room ambient temperature. The plate was then aspirated and rinsed with deionized water to remove all soluble dye. Absorbances were read using a Titertek Plate Reader at 595 nm.

Effects of Additives In the Polystyrene

Experiments were conducted using polystyrene pellets from a lot without added zinc stearate, mineral oil, or wax. The native pellets were reduced to a powder by dry grinding in a coffee grinder. The recovered powder was washed with isopropanol on a Buchner funnel, air dried, and sieved to various mesh sizes. The ProNectin®F was deposited onto the polystyrene powder of 60–80 mesh using a modified vortex dilution technique. The polymer powders (5.0 g) were slurried in 15 ml of water. While vortexing, a solution of ProNectin®F in formic acid (1 mg/15 ml) was added in one portion. While vortexing, water (30 ml) was added over about 60 seconds.

Several sample films from each lot of powder were compression molded from 250 mg of coated polystyrene between 304 stainless steel sheets using a Carver press with plattens heated electrically to 150° C. and a maximum force of 1500 kilograms for 3–5 seconds. Four sample disks for cell attachment assay were taken from the center of each of three films using a standard 7 mm "one-hole-punch". All cell attachment assays were conducted on a single 96-well plate according to standard protocols.

TABLE 3

Optical Densities of Cell Attachment Assays on Compression Molded Films with PnF.

| Sample | PnF [ppm] | Polymer Disks | N | OD [mean] | ±σ | CV |
|---|---|---|---|---|---|---|
| Bare Plate | | | 8 | 0.000 | ±0.003 | n/a |
| Bare Plate | | Solution coated 1 μg-PnF/ml | 8 | 0.797 | ±0.037 | 5% |
| 102,028-1 | | PS[1R3-C0] Solution coated 1 μg-PnF/ml | 8 | 0.669 | ±0.070 | 10% |
| 102,028-9 | | PS[6R3-C7] Solution coated 1 μg-PnF/ml | 8 | 0.681 | ±0.074 | 11% |
| 102,028-1 | 000 | PS [Amoco 1R3-C0] | 8 | 0.000 | ±0.010 | n/a |
| 102,028-9 | 000 | PS [Amoco GR3-C7] | 8 | 0.000 | ±0.028 | n/a |
| 102,028-2 | 200 | PS [Amoco 1R3-C0] | 8 | 0.557 | ±0.046 | 8% |
| 102,028-10 | 200 | PS [Amoco 6R3-C7] | 8 | 0.106 | ±0.117 | 111% |

In the above table, the polystyrene sample [Amoco IR3-C0] has no added zinc stearate or added waxes, while the polystyrene sample [Amoco GR3-C7] has 1700 ppm zinc stearate and added waxes.

After the disks were mounted on the tissue culture plate with silicone grease, a matrix of optical densities was measured. The optical densities reported in the above table were corrected on a well-by-well basis for the variations in optical densities arising from the "cloudiness" of the inserted polystyrene disks and from the silicone grease used to affix the disks to the bottoms of the wells. Each well thus became its own control. The optical densities were also corrected for the fact that the disks tend to pick up a little color during the staining process with the amidoblack chromophore. The cell attachment experiment in this case was the standard assay for fibronectin activity using VERO cells. In order to further validate this particular assay, one bare lane was coated with ProNectin®F directly onto the polystyrene plate using standard solution coating methods. This acts as a check on the "temperament" of the particular batch of VERO cells used to conduct the assay.

The performance of ProNectin®F which was coated from solution onto polystyrene surfaces was unaffected by the presence or absence of processing aids added to the underlying polystyrene by the manufacturer. On the other hand, the performance of ProNectin®F which was dispersed into polystyrene powder and compression molded into films was seriously reduced by the presence of such processing aids. In the case of Amoco GR3-C7, the most likely cause of the degraded performance is believed to be the zinc stearate added as a mold release agent.

ProNectin®F, SLP3, and P-85 Surfactant

Polystyrene pellets without added zinc stearate, lubricants, or waxes (Amoco IR3-C0) was ground to a powder in a standard laboratory Waring blender using neat isopropanol as the slurrying agent. The recovered powder was further washed with isopropanol on a Buchner funnels, dried in air, and sieved to >100 mesh using American Standard stainless steel sieves. The additives used in these experiments were the protein polymers ProNectin®F and SLP3. The surfactant used was Pluronic P-85 from BASF Corporation. The protein polymers SLP3 and SLPF share a common backbone with the exception that SLPF includes a cell binding domain. Thus SLP3 serves as a negative control for the performance of the SLPF. The various additives were dissolved in 30 ml of formic acid (85%), slurried with 10 g of sieved polystyrene powder >100 mesh, and concentrated to dryness on a rotary evaporator. Several sample films from each lot of powder were compression molded from 250 mg of coated polystyrene between 304 stainless steel sheets using a Carver press with plattens heated electrically to 150° C. and a maximum force of 1500 Kg for 3–5 seconds. The total time for the molding cycle was about 15 seconds. Four sample disks for cell attachment assay were taken from the center of each film using a standard 7 mm "one-hole" paper punch. All cell attachment assays were conducted on a single 96-well tissue culture plate using the cell attachment assay protocols described above.

TABLE 4

Cell Attachment Assays

| | PnF [ppm] | P-85 [ppm] | SLP3 [ppm] | N | OD [mean] | ±σ | CV |
|---|---|---|---|---|---|---|---|
| 102,017-00 | Solution coated with 100 µl of 1 µg-PnF/ml | | | 8 | 0.608 | ±0.159 | 26% |
| 102,017-01 | 0 | 0 | 400 | 6 | 0.122 | ±0.034 | 28% |
| 102,017-02 | 0 | 400 | 400 | 6 | 0.116 | ±0.020 | 17% |
| 102,017-03 | 400 | 0 | 0 | 8 | 0.642 | ±0.079 | 12% |
| 102,017-04 | 50 | 100 | 0 | 8 | 0.166 | ±0.033 | 20% |
| 102,017-05 | 800 | 100 | 0 | 8 | 0.513 | ±0.144 | 28% |
| 102,017-06 | 200 | 200 | 0 | 8 | 0.116 | ±0.027 | 24% |
| 102,017-07 | 0 | 400 | 0 | 8 | 0.091 | ±0.020 | 22% |
| 102,017-08 | 100 | 400 | 0 | 8 | 0.100 | ±0.017 | 17% |
| 102,017-09 | 400 | 400 | 0 | 8 | 0.101 | ±0.017 | 17% |
| 102,017-10 | 200 | 800 | 0 | 8 | 0.095 | ±0.015 | 16% |
| 102,017-11 | 50 | 1600 | 0 | 6 | 0.115 | ±0.033 | 28% |
| 102,017-12 | 800 | 1600 | 0 | 6 | 0.178 | ±0.048 | 27% |

Optical densities were measured at 595 nm, which is to say that attached cells stain with a blue color. There exists a modest background optical absorbance in these measurements due to a slight opacity of the inserted disks as well as the presence of the silicone grease used as adhesive. The measured optical densities of the 102,017-02 and -03 samples serve as a measure of this background absorbance. As can be seen in the data in the above table, the performance of the disks from sample 102,017-03 is indistinguishable from that of Polystyrene disks which were coated with ProNectin®F from solution in aqueous lithium perchlorate. Only low levels of the P-85 surfactant could be tolerated in combination with the ProNectin®F without seriously degrading the cell attachment performance of the ProNectin®F. Again, these results demonstrated the sensitivity of the cell attachment performance of the ProNectin®F to interferences from additives present in the polystyrene.

Deposition of ProNectin®F onto Polystyrene by Evaporative Coating

Experiments were conducted using Polystyrene pellets (Amoco IR3-C0) from a lot without added zinc stearate, mineral oil, or wax. The native pellets were ground to a powder using neat isopropanol as the slurrying agent in a miniature Waring blender. The recovered powder was further washed with isopropanol on a Buchner funnel, air dried, and sieved to various mesh sizes. The ProNectin®F was dissolved in 30 ml of formic acid, slurried with 10 g of sieved polystyrene powder, and concentrated to dryness on a rotary evaporator. Several sample films from each lot of powder were compression molded from 250 mg of coated polystyrene between 304 stainless steel sheets using a Carver press with plattens heated electrically to 150° C. and a maximum force of 1500 kilograms for 3–5 seconds. Four sample disks for cell attachment assay were taken from the center of each of three films using a standard 7 mm "one-hole-punch". A cell attachment assay was conducted on a single 96-well plate using the standard protocol described above.

TABLE 5

Optical Densities of Cell Attachment Assays On Compression Molded PS With PnF

| | PnF [ppm] | PS Powder mesh range | N | OD [mean] | ±σ | CV |
|---|---|---|---|---|---|---|
| Bare Plate | Optical blank, no cells | | 8 | 0.037 | ±0.002 | 4% |
| Bare Plate | Solution coated with 100 µl of 1 µg/-PnF/ml | | 8 | 0.573 | ±0.024 | 4% |
| 103-64-00 | PS Optical & Stain blank; no cells | | 8 | 0.085 | ±0.035 | 41% |
| 103-64-00 | PS solution coated with 100 µl 1 µg/-PnF/ml | | 8 | 0.600 | ±0.075 | 13% |
| 103-64-J | 150 | 20–40 | 8 | 0.500 | ±0.061 | 12% |
| 102-17-03 | 400 | >100 | 8 | 0.493 | ±0.069 | 14% |
| 103-64-A | 400 | >100 | 8 | 0.461 | ±0.045 | 10% |
| 103-64-B | 200 | >100 | 8 | 0.352 | ±0.086 | 24% |
| 103-64-C | 150 | >100 | 8 | 0.181 | ±0.055 | 30% |
| 103-64-F | 150 | 60–80 | 8 | 0.471 | ±0.097 | 20% |
| 103-64-G | 150 | 20–40 | 8 | 0.353 | ±0.074 | 21% |
| 103-64-D | 100 | >100 | 8 | 0.115 | ±0.056 | 49% |
| 103-64-E | 50 | >100 | 8 | 0.012 | ±0.049 | 408% |

After the polystyrene disks were mounted on the tissue culture plate with silicone grease, a matrix of optical densities was measured. The optical densities reported in the above table were corrected on a well-by-well basis for the variations in optical densities arising from the "cloudiness" of the inserted polystyrene disks and from the silicone grease used to affix the disks to the bottoms of the wells. Each well thus became its own control. The optical densities were also corrected for the fact that the polystyrene disks tend to pick up a little color during the staining process with the amidoblack.

Data from samples prepared with >100 mesh powder was especially well behaved with cell attachment performance decreasing monotonically with the concentration of applied ProNectin®F.

At 400 ppm PnF compression molded into this polystyrene powder, the performance of the disks was statistically indistinguishable from PnF at 1 µg/ml solution coated onto the same disks or onto the bare plate. Below 250–300 ppm, the performance began to fall off.

Strangely enough, the above data showed that PnF at 150 ppm on 60–80 mesh polystyrene powder performed as well as PnF at 400 ppm on >100 mesh. Thus the mesh size of the polystyrene powder appeared to be a determinant of the performance when ProNectin®F was deposited onto the polystyrene by evaporative coating.

Deposition of ProNectin®F onto Polyethylene by Evaporative Deposition

Experiments were conducted using low density polyethylene (PE) powder commercially available from Aldrich Chemical Company as catalog number 18,189-7. The powder was of unknown composition with respect to processing aids or stabilizers added by the manufacturer. In order to reduce the possibility of interferences by these additives, the PE powder was subjected to exhaustive extraction with boiling isopropanol for 24 hours in a Soxhlet apparatus. Recovered polyethylene powder was air dried before use. The ProNectin®F was dissolved in 30 ml of formic acid, slurried with 10 g of PE powder, and concentrated to dryness on a rotary evaporator. Several sample films from each lot of powder were compression molded from 250 mg of coated polyethylene between 304 stainless steel sheets using a Carver press with plattens heated electrically to 150° C. Four sample disks for cell attachment assay were taken from the center of each of three films using a standard 7 mm "one-hole-punch". A cell attachment assay was conducted on a single 96-well plate using the standard protocol described above.

TABLE 6

Optical Densities of Cell Attachment Assays On Compression Molded PE With PnF.

| ProNectin ® F On Polyethelene Powder | | N | OD [mean] | ±σ | CV |
|---|---|---|---|---|---|
| Bare Plate | Optical blank | 8 | 0.032 | ±0.002 | 6% |
| Bare Plate | Solution coated with 100 µl of 1 µg-PnF/ml | 8 | 0.721 | ±0.022 | 3% |
| 103,064-00 | Solution coated with 100 µl of 1 µg-PnF/ml | 8 | 0.591 | ±0.052 | 9% |
| 103,064-01 | 600 ppm | 8 | 0.092 | ±0.060 | 65% |
| 103,064-02 | 400 ppm | 8 | 0.085 | ±0.061 | 72% |
| 103,064-03 | 200 ppm | 8 | 0.169 | ±0.100 | 59% |
| 103,064-04 | 150 ppm | 8 | 0.138 | ±0.084 | 75% |
| 103,064-05 | 100 ppm | 8 | 0.084 | ±0.063 | 75% |
| 103,064-06 | 50 ppm | 8 | 0.066 | ±0.067 | 102% |
| 103,064-00 | 00 ppm | 8 | 0.000 | ±0.036 | n/a |

After the disks were mounted on the tissue culture plate with silicone grease, a matrix of optical densities was measured. The optical densities reported in the above table were corrected on a well-by-well basis for the variations in optical densities arising from the "cloudiness" of the inserted polyethylene disks and from the silicone grease used to affix the disks to the bottoms of the wells. Each well thus became its own control. The optical densities were also corrected for the fact that the disks tend to pick up a little color during the staining process with the amidoblack dyestuff. In order to further validate this particular assay, one bare lane was coated with ProNectin®F directly onto the polystyrene plate using standard solution coating methods.

Clearly, ProNectin®F which was evaporatively coated onto polyethylene powder and compression molded into films was active in a cell attachment assay using VERO cells. The degree of attachment activity is lower compared to that observed on polystyrene. The difference in performance between polystyrene and polyethylene may have been due to additives in the polyethylene which were not removed in the washing step.

Deposition of ProNectin®F onto Polypropylene and Polymethylmethacrylate by Vortex Dilution.

Polypropylene non-woven fabric was recovered from the liner of a disposable diaper and washed exhaustively with isopropanol in Soxhlet apparatus for 24 hours. This fabric represents a conveniently available source polypropylene with a high surface area suitable for coating with ProNectin®F. Coating was conducted using the modified vortex dilution technique as described in the section entitled "Effects of Additives in the Polystyrene". Polymethylmethacrylate (Aldrich Chemical Company catalog number 18,224-9)as a medium molecular weight powder was used without additional purification. Coating was conducted using the modified vortex dilution technique.

Several sample films from each lot of coated polymer were compression molded from 250 mg samples between 304 stainless steel sheets using a Carver press with plattens heated electrically to 150° C. and a maximum force of 1500 kilograms for 3–5 seconds. Four sample disks for cell attachment assay were taken from the center of each of three films using a standard 7 mm "one-hole-punch". A cell attachment assay was conducted on a single 96-well plate using the standard protocol described above.

TABLE 7

Deposition of ProNectin ® F onto Polypropylene and Polymethylmethacrylate.

| Sample | PnF [ppm] | Polymer Disks | N | OD [mean] | ±σ | CV |
|---|---|---|---|---|---|---|
| Bare Plate | | | 8 | 0.000 | ±0.003 | n/a |
| Bare Plate | Solution coated 1 µg-PnF/ml | | 8 | 0.797 | ±0.797 | 5% |
| 102,028-1 | 000 | PS [Amoco IR3-C0] | 8 | 0.000 | ±0.010 | n/1 |
| 102,028-2 | 200 | PS [Amoco IR3-C0] | 8 | 0.557 | ±0.046 | 8% |
| 102,028-7 | 000 | Poly[Methyl Methacrylate] | 8 | 0.000 | ±0.038 | n/1 |
| 102,028-8 | 200 | Poly[Methyl Methacrylate] | 8 | 0.435 | ±0.050 | 11% |
| 102,028-11 | 000 | Polypropylene | 8 | 0.000 | ±0.042 | n/a |
| 102,028-12 | 230 | Polypropylene | 8 | 0.252 | ±0.128 | 51% |

These results showed that ProNectin®F could be compression molded into polypropylene and polymethylmethacrylate films. Neither the polypropylene nor the polymethylmethacrylate was of known composition with respect to low level concentrations of additives and surfactants. These particular samples of polymers were used because they were readily available and not because they were known to be optimal for this application. In any case, these samples of polymers showed cell attachment activity when compression molded with ProNectin®F.

Effect of Deposition Methods and Mesh Size

Experiments were conducted using polystyrene pellets (Amoco IR3-C0) from a lot without added zinc stearate, mineral oil, or wax. The native pellets were reduced to a powder by dry grinding in a coffee grinder. The recovered powder was washed with isopropanol on a Buchner funnel, air dried, and sieved to various mesh sizes. The ProNectin®F was deposited onto the polystyrene powders using one of three methods: evaporation of the formic acid in the absence of water, referred to as "Dry" rotovap; evaporation of the formic acid after the addition of 5 ml of water, referred to as "Wet" rotovap; and dilution of the formic acid with water under vortexing conditions, referred to as "Vortex" dilution. Several sample films from each lot of powder were compression molded from 250 mg of coated polystyrene between 304 stainless steel sheets using a Carver press with plattens heated electrically to 150° C. and a maximum force of 1500 kilograms for 3–5 seconds. Four sample disks for cell attachment assay were taken from the center of each of three films using a standard 7 mm "one-hole-punch". A cell attachment assay was conducted on a single 96-well plate using the standard protocol described above.

TABLE 8

Optical Densities of Cell Attachment Assays On Compression Molded PS With PnF.

| Sample | PnF [ppm] | Deposition Method | PS Powder mesh range | N | OD [mean] | ±σ | CV |
|---|---|---|---|---|---|---|---|
| 103,065-00 | | Optical blank, cells & stain | | 8 | 0.000 | ±0.032 | n/a |
| 103,065-00 | | Solution coated with 100 µl of 1 µg-PnF/ml | | 8 | 0.655 | ±0.099 | 15% |
| 103,065-A | 150 | Dry Rotovap | >100 | 8 | 0.112 | ±0.049 | 44% |
| 103,065-B | 150 | Wet Rotovap | >100 | 8 | −0.008 | ±0.051 | n/a |
| 103,065-C | 150 | Vortex Dil'n | >100 | 8 | 0.468 | ±0.112 | 24% |
| 103,065-D | 150 | Dry Rotovap | 60–80 | 8 | 0.151 | ±0.045 | 30% |
| 103,065-E | 150 | Wet Rotovap | 60–80 | 8 | 0.335 | ±0.083 | 25% |
| 103,065-F | 150 | Vortex Dil'n | 60–80 | 8 | 0.532 | ±0.071 | 13% |
| 103,065-G | 150 | Dry Rotovap | 20–40 | 8 | 0.239 | ±0.044 | 18% |
| 103,065-H | 150 | Wet Rotovap | 20–40 | 8 | 0.102 | ±0.081 | 79% |
| 103,065-I | 150 | Vortex Dil'n | 20–40 | 8 | 0.410 | ±0.043 | 10% |
| 103,065-J | 150 | Wet Rotovap | 40–60 | 8 | 0.149 | ±0.72 | 408% |

After the disks were mounted on the tissue culture plate with silicone grease, a matrix of optical densities was measured. The optical densities reported in the above table were corrected on a well-by-well basis for the variations in optical densities arising from the "cloudiness" of the inserted polystyrene disks and from the silicone grease used to affix the disks to the bottoms of the wells. Each well thus became its own control. The optical densities were also corrected for the fact that the disks tend to pick up a little color during the staining process with the amidoblack. In order to further validate this particular assay, one bare lane was coated with ProNectin®F directly onto the polystyrene plate using standard solution coating methods. This acts as a check on the "temperament" of the particular batch of cells used to conduct the assay.

The data in Table 8 showed that the most efficient utilization of ProNectin®F coated onto polystyrene powders comes about using the vortex dilution method. The mesh size of the polystyrene powder did not seem to be a major determinant of the outcome of the vortex dilution coating process. The use of mixed mesh polystyrene powders eased the preparation of these powders because the useable fraction of ground powder increases with the broader mesh range.

Water present during evaporative deposition had an effect on the outcome of the coating process. This observation could explain the variablility observed in some of the evaporative coating experiments. Variable amounts of water could enter the rotary evaporator from room ambient water vapor through accidental leaks or through sparging of the rotary evaporator apparatus with air during the evaporation process.

Deposition of ProNectin®F onto Polystyrene by Vortex Dilution Coating

Experiments were conducted using polystyrene (PS) pellets (Amoco IR3-C0) from a lot without added zinc stearate, mineral oil, or wax. The native pellets were ground to a powder in a miniature Waring blender without suspending solvent. The recovered powder was washed with isopropanol on a Buchner funnel, air dried, and sieved to >20 mesh. The ProNectin®F was dissolved in 15 ml of formic acid, slurried with 5 g of sieved polystyrene powder, agitated on a vortex mixer, and diluted with 45 ml of deionized water. The recovered polystyrene powder was collected on a Buchner funnel and dried in air. Several sample films from each lot of powder were compression molded from 250 mg of coated polystyrene between 304 stainless steel sheets using a Carver press with plattens heated electrically to 150° C. and a maximum force of 1500 kilogmms for 3–5 seconds. Four sample disks for cell attachment assay were taken from the center of each of three films using a standard 7 mm "one-hole-punch". A cell attachment assay was conducted on a single 96-well plate using the standard protocol described above.

TABLE 9

Optical Densities of Cell Attachment Assays On Compression Molded PS With PnF

| Sample | PnF [ppm] | PSPowder mesh range | N | OD [mean] | ±σ | CV |
|---|---|---|---|---|---|---|
| Bare Plate | Optical blank, no cells or stain | | 8 | 0.037 | ±0.001 | 3% |
| Bare Plate | Solution coated with 100 µl of 1 µg/-PnF/ml | | 8 | 0.799 | ±0.026 | 3% |
| 103-66-00 | PS Optical blank, no cells or stain | | 8 | 0.007 | ±0.016 | 229% |
| 103-66-00 | PS blank, cells and stain | | 8 | 0.022 | ±0.012 | 55% |
| 103-66-00 | Solution coated with 100 µl of 1 µg/-PnF/ml | | 8 | 0.747 | ±0.052 | 7% |
| 103-66-A | 300 | >20 | 8 | 0.516 | ±0.048 | 9% |
| 103-66-B | 250 | >20 | 8 | 0.641 | ±0.073 | 11% |
| 103-66-C | 200 | >20 | 8 | 0.627 | ±0.068 | 11% |
| 103-66-D | 150 | >20 | 8 | 0.650 | ±0.057 | 9% |
| 103-66-E | 100 | >20 | 8 | 0.544 | ±0.067 | 12% |
| 103-66-F | 50 | >20 | 8 | 0.592 | ±0.060 | 10% |

After the polystyrene disks were mounted on the tissue culture plate with silicone grease, a matrix of optical densities was measured. The optical densities reported in the above table were corrected on a well-by-well basis for the variations in optical densities arising from the "cloudiness" of the inserted polystyrene disks and from the silicone grease used to affix the disks to the bottoms of the wells. Each well thus became its own control. The optical densities were also corrected for the fact that the polystyrene disks tend to pick up a little color during the staining process with the amidoblack.

ProNectin®F retained its activity down to 50 ppm. The combination of mixed mesh powders with vortex dilution deposition was extremely efficacious in depositing PnF in active form.

The reason for the reduced effectiveness of evaporative deposition compared to vortex deposition could be hydrolysis of the protein. The efficacy of vortex deposition bodes very well for the economics of the process.

Compression Molding of Polystyrene Containing ProNectin L

Experiments were conducted using polystyrene pellets from a lot without added zinc stearate, mineral oil, or wax. The native pellets were reduced to a powder by dry grinding in a coffee grinder. The recovered powder was washed with isopropanol on a Buchner funnel, air dried, and sieved to various mesh sizes. The ProNectin®L (PnL or SLPL 3.0) was deposited onto the polystyrene powder of 60–80 mesh using the vortex dilution technique. Several sample films from each lot of powder were compression molded from 250 mg of coated polystyrene between 304 stainless steel sheets using a Carver press with plattens heated electrically to 150° C. and a maximum force of 1500 kilogmms for 3–5 seconds. Four sample disks for cell attachment assay were taken from the center of each of three films using a standard 7 mm "one-hole-punch". A cell attachment assay was conducted on a single 96-well plate as described below.

a test disk was added 25 µl of the silicone adhesive solution. The plate was then dried overnight in a vacuum oven at 40° C. One lane of the plate, as a positive control, was solution coated with ProNectin®L using the standard protocols described above. Best results were obtained when all wash and aspiration steps were performed using a Biotek 403H automated plate washer with settings: dispense height=10; plate height=100; dispense volume=200 µl; and number of washes=2.

While the positive control lane was being solution coating with ProNectin®L, the 7 mm diameter test disks were placed into 5 dram vials and washed 3 times with 5 ml of 1× calcium-magnesium free phosphate buffered saline (cmf PBS). The test disks were then placed into each well and gently pressed into the silicone grease which had been layered on the bottom of the well. After mounting the test disks into the plate, they were washed twice with 100 µl of 1× cmf PBS. At this time, the background absorbances were

TABLE 10

Optical Densities of Cell Attachment Assays On Compression Molded PS With ProNectin ® L.

|  | PnL [ppm] | Deposition Method | PS Powder mesh range | N | OD [mean] | ±σ | CV |
|---|---|---|---|---|---|---|---|
| Bare plate | Optical blank, cell & stain | | | 8 | 0.000 | ±0.014 | n/a |
| Bare plate | Solution coated with 100 µl of 1 µg-PnF/ml | | | 8 | 0.767 | ±0.106 | 14% |
| 103,067-00 | PS optical blank, cells & stain | | | 6 | 0.000 | ±0.016 | n/a |
| 103,067-00 | PS, solution coated with 100 µl of 1 µg-PnF/ml | | | 8 | 0.797 | ±0.144 | 18% |
| 103,065-A | 500 | Vortex | 60–80 | 8 | 0.052 | ±0.038 | 73% |
| 103,065-B | 550 | Vortex | 60–80 | 8 | 0.043 | ±0.043 | 100% |
| 103,065-C | 150 | Vortex | 60–80 | 8 | 0.046 | ±0.031 | 67% |
| 103,065-C1 | 150 | Vortex | 60–80 | 6 | 0.342 | ±0.106 | 31% | the disks to the bottoms of the wells. Each well thus became its own control. The optical densities were also corrected for the fact that the disks tend to pick up a little color during the staining process with the amidoblack. The cell attachment experiment in this case was the standard assay for laminin activity using RD-P56 cells, described below. In order to further validate this particular assay, one bare lane was coated with ProNectin®L directly onto the polystyrene plate using standard solution coating methods. This acts as a check on the "temperament" of the particular batch of RD-P56 cells used to conduct the assay.

This data showed that ProNectin L could survive the thermal history of the compression molding process. After drying in air, the vortex dilution coated polystyrene powders retained a slight odor of formic acid. The sample 103,067-C1 was compression molded as it stood. The other samples were sparged with a stream of dry nitrogen until all odor of formic acid was removed. It could be that the IKVAV sequences of the ProNectin L in sample 103,067-C1 were stabilized towards thermal degradation by neutralization of the lysines with this residual formic acid. In particular, more reproducible results are obtained when non-volatile acids such as toluene sulfonic acid are added to the compression molding mixtures.

Attachment Assay Using RD-P56 Cells

The silicone grease "adhesive" used to affix compression molded test disks to the tissue culture plates was prepared by diluting Dow Corning High Vacuum Grease with cyclohexane to a final concentration of 25% w/v, centrifuging to compact the silica filler, and retaining the supernatant. To each well of a 96-well tissue culture plate which is to receive read using a Titertek Plate Reader at 595 nm. Blocking solution (2 mg of bovine serum albumin per milliliter of cmf PBS), 100 µl, was added to each well and incubated for 30 minutes at 37° C. The blocking solution was aspirated and the plate rinsed once with cmf PBS. RD-P56 cells, $1 \times 10^5$ cells, were added to each well using culture media without fetal bovine serum and the plate incubated for 1 hour 37° C. The media containing the cells was aspirated and the plate rinsed twice with cmf PBS. Fixative solution (3.7% formaldehyde in 1× cmf PBS) was added to each well and incubated for 20 minutes at room ambient temperature. The fixative solution was aspirated and the plate was rinsed once with cmf PBS. Staining solution (0.1% amido black in 40% methanol-10% acetic acid) was added, and the plate was incubated for 15 minutes at room ambient temperature. The plate was then rinsed with deionized water to remove all soluble dye. The plate was dried over night at room ambient temperature. Elution buffer (10% aqueous sodium dodecyl sulfate) was added and the absorbance read using the Titertek Plate Reader at 595 nm.

Reproducibility of Coatings Deposited by Vortex Dilution
Experiments were conducted using polystyrene pellets (Amoco IR3-C0) from a lot without added zinc stearate, mineral oil, or wax. The native pellets were ground to a powder in a miniature Waring blender without suspending solvent. The recovered powder was washed with isopropanol on a Buchner funnel, air dried, and sieved to >20 mesh. The ProNectin®F was dissolved in 15 ml of formic acid, slurried with 5 g of sieved polystyrene powder, agitated on a vortex mixer, and diluted with 45 ml of deionized water. The recovered polystyrene powder was collected on a Buchner funnel and dried in air. Three independent preparations of polystyrene powder coated with ProNectin®F were conducted and sampled individually for compression molding. The three preparations were combined, physically mixed, and again sampled for compression molding.

Several sample films from each lot of powder were compression molded from 250 mg of coated polystyrene between 304 stainless steel sheets using a Carver press with plattens heated electrically to 150° C. and a maximum force of 1500 kilogmms for 3–5 seconds. Four sample disks for cell attachment assay were taken from the center of each of three films using a standard 7 mm "one-hole-punch". A cell attachment assay was conducted on a single 96-well plate using the standard protocol described above.

TABLE 11

Optical Densities of Cell Attachment Assays on Compression Molded PS with PnF.

| | PnF [ppm] | PS powder mesh range | N | OD [mean] | ±σ | CV |
|---|---|---|---|---|---|---|
| Bare Plate | Solution coated with 100 µl of 1 µg/-PnF/ml | | 8 | 0.547 | ±0.019 | 3% |
| 103-069-00 | PS Optical blank, no cells or stain | | 7 | 0.000 | ±0.024 | n/a |
| 103-069-00 | PS blank, cells and stain | | 8 | 0.555 | ±0.036 | 6% |
| 103-069-A | 200 | >20 | 8 | 0.473 | ±0.031 | 9% |
| 103-069-B | 200 | >20 | 8 | 0.526 | ±0.046 | 7% |
| 103-069-C | 200 | >20 | 8 | 0.521 | ±0.071 | 14% |
| 103-069-D | 200 | >20 | 7 | 0.535 | ±0.033 | 6% |

The data in Table 11 showed that multiple preparations of a coated polystyrene powder gave the same result. The coating process appeared reproducible. The mean optical density for preparations A, B, C & D, which is [A+B+C], was 0.520±0.047. The results in Table 11 showed that the application of ProNectin®F to polystyrene powder can be accomplished with high reproducibility on a batch-to-batch basis. Establishing such reproducibility is important to the design of coating processes at a commercial scale.

Usable Dispersing Agents

Experiments were conducted using polystyrene pellets (Amoco IR3-C0) from a lot without added zinc stearate, mineral oil, or wax. The native pellets were ground to a powder in a miniature Waring blender without suspending solvent. The recovered powder was washed with isopropanol on a Buchner funnel, air dried, and sieved to >20 mesh. The ProNectin®F was dissolved in 15 ml of formic acid, slurried with 5 g of sieved polystyrene powder, agitated on a vortex mixer, and diluted with 45 ml of deionized water. The recovered polystyrene powder was collected on a Buchner funnel and dried in air.

Polystyrene powder which was precoated with ProNectin®F was then challenged with a wash with isopropanol alone and in combination with reagents which are potentially useful as agents for the dispersal of ProNectin®F into polystyrene melts. The reagents, each at 200 ppm in isopropanol (103,069-E), were phenyltriethoxysilane (103,069-F), tetraisopropoxytitanium (IV) (103,069-G), isopropoxytris isosteroyl titanate (Kenrich KR-TTS) (103,069-I), neopentyl(diallyl)oxy-[tris(dioctyl)pyrophosphato]titanate (Kenrich LICA-38) (103,069-H).

Preparation of compression molded film samples and a cell attachment assay were conducted using standard protocols described above.

TABLE 12

Optical Densities of Cell Attachment Assays on Compression Molded PS with PnF.

| | PnF [ppm] | PS Powder mesh range | N | OD [mean] | ±σ | CV |
|---|---|---|---|---|---|---|
| Bare Plate | Solution coated with 100 µl of 1 µg/-PnF/ml | | 8 | 0.547 | ±0.019 | 3% |
| 103,069-00 | PS Optical blank, no cells or stain | | 7 | 0.000 | ±0.024 | n/a |
| 103,069-00 | PS blank, cells and stain | | 8 | 0.555 | ±0.036 | 6% |
| 103,069-A | 200 | | 8 | 0.473 | ±0.031 | 9% |
| 103,069-E | 200 | | 8 | 0.482 | ±0.073 | 15% |
| 103,069-F | 200 | | 7 | 0.512 | ±0.040 | 8% |
| 103,069-G | 200 | | 8 | 0.509 | ±0.048 | 10% |
| 103,069-H | 200 | | 7 | 0.490 | ±0.067 | 14% |
| 103-069-I | 200 | | 8 | 0.510 | ±0.042 | 8% |

The data in table 12 showed that these dispersing agents did not interfere with the cell attachment function of the ProNectin®F when they were added to the coated polystyrene powder at these concentrations. These four dispersing agents thus may be considered as aids for achieving improved mixing of the ProNectin®F throughout the polystyrene melt during a thermolding process.

Thermal Stress Matrix for Unstabilized ProNectin®F

Experiments were conducted using polystyrene pellets from a lot without added zinc stearate, mineral oil, or wax. The native pellets were ground to a powder in a miniature Waring blender without suspending solvent. The recovered powder was washed with isopropanol on a Buchner funnel, air dried, and sieved to >20 mesh. The ProNectin®F (1.0 mg) was dissolved in 15 ml of formic acid, slurried with 5 g of sieved polystyrene powder, agitated on a vortex mixer, and diluted with 45 ml of deionized water. The recovered polystyrene powder was collected on a Buchner funnel and dried in air without agitation. This powder was designated as having been coated at 200 ppm.

A sample (2.0 g) of polystyrene powder coated with ProNectin®F (200 ppm) was placed into a Pyrex glass tube (16mm×100 mm); sealed with a rubber septum cap, sparged with nitrogen, and heated in a thermostatted oil bath preheated to the required temperature for varying lengths of time. Several sample films from each lot of powder were compression molded from 250 mg of coated polystyrene between 304 stainless steel sheets using a Carver press with plattens heated electrically to 150° C. and a maximum force of 1500 kilogmms for 3–5 seconds. Four sample disks for cell attachment assay were taken from the center of each of three films using a standard 7 mm "one-hole-punch". A cell attachment assay was conducted on a single 96-well plate using the standard protocol described above.

TABLE 13

Optical Densities of Cell Attachment Assays.

| | PnF [ppm] | Time [min] | Temp. [°C.] | N | OD [mean] | ±σ | CV |
|---|---|---|---|---|---|---|---|
| Bare Plate | Solution coated with 100 µl of 1 µg/-PnF/ml | | | 8 | 0.628 | ±0.008 | 1% |
| 103-075-1 | 200 | 1/4 | 150° | 8 | 0.530 | ±0.099 | 19% |
| 103-075-2 | 200 | 5 | 150° | 8 | 0.488 | ±0.069 | 14% |
| 103-075-3 | 200 | 80 | 150° | 8 | 0.200 | ±0.106 | 53% |
| 103-075-4 | 200 | 20 | 175° | 8 | 0.083 | ±0.042 | 51% |
| 103-075-5 | 200 | 10 | 200° | 8 | 0.066 | ±0.036 | 55% |
| 103-075-6 | 200 | 20 | 200° | 8 | 0.036 | ±0.031 | 86% |

TABLE 13-continued

Optical Densities of Cell Attachment Assays.

| | PnF [ppm] | Time [min] | Temp. [°C.] | N | OD [mean] | ±σ | CV |
|---|---|---|---|---|---|---|---|
| 103-075-7 | 200 | 40 | 200° | 8 | 0.010 | ±0.020 | 200% |
| 103-075-8 | 200 | 20 | 225° | 8 | 0.008 | ±0.011 | 138% |
| 103-075-9 | 200 | 5 | 250° | 8 | 0.011 | ±0.014 | 127% |
| 103,075-10 | 200 | 40 | 250° | 8 | 0.0003 | ±0.011 | n/a |
| 103,075-11 | 200 | 10 | 275° | 8 | 0.0063 | ±0.015 | n/a |

After the polystyrene disks were mounted on the tissue culture plate with silicone grease, a matrix of optical densities was measured. The optical densities reported in the above table were corrected on a well-by-well basis for the variations in optical densities arising from the "cloudiness" of the inserted polystyrene disks and from the silicone grease used to affix the disks to the bottoms of the wells. Each well thus became its own control. The optical densities were also corrected for the fact that the polystyrene disks tend to pick up a little color during the staining process with the amidoblack.

The performance of the compression molded disks of polystyrene in the cell attachment assay decreased with increasing time and with increasing temperature in a complex manner. The amount of ProNectin®F required in the initial formulation will be dictated by the required performance of the final article and by the time-temperature history of the injection molding process.

The time-temperature experiments represented a response surface which could be fitted by multivariate regression analysis. A model was defined which assumes a semi-first order reaction for thermal degradation with the rate constant being exponential in temperature. The fit of this model was $R^2 = 0.963$, and the equation had the satisfying property of fitting only three adjustable parameters to the 11 data points. The following parameters can be added together to form an equation which can be used to interpolate points on the time-temperature response surface.

Parameter estimates for $Ln[Ln(A_0/A)]$ $R^2 = 0.963$

| Term | Coefficient | Std Error | t Ratio | Prob > |t| |
|---|---|---|---|---|
| Intercept | 12.256021 | 1.49242 | 8.21 | 0.0000 |
| Ln [t] | 0.7049276 | 0.08461 | 8.33 | 0.0000 |
| 1/°K. | −6429.016 | 672.61 | −9.56 | 0.0000 |

Relationship of Solution Concentrations to Surface Deposition

Films were compression molded from polystyrene pellets (Amoco IR3-C0) and cut into strips 1 cm×2 cm. In order to reduce the fluorescent background due to low level contaminants as much as possible, the films were extracted in concentrated hydrochloric acid for 18 hours at 80° C. The disks were rinsed in deionized water and solution coated with ProNectin®F using a solution of PnF (1 mg/ml) in 88% formic acid serially diluted out to the final concentrations with 1× phosphate buffered saline. Polystyrene films were left in contact with the diluted coating solutions for 2 hours on a nutator to provide agitation. The films were recovered, rinsed in deionized water, and air dried. Proteins on the surface of the each piece of film were hydrolysed by exposure to the vapors of constant boiling hydrochloric acid in an evacuated container for 18 hours at 80° C. The vials were opened and placed in a vacuum oven at 40° C. for 2 hours to remove water and hydrogen chloride. The residue of hydrolysed amino acids was dissolved using 1 ml of 100 mM pH9 borate buffer. Fluorescence was developed by adding 1 ml of a solution of fluorescamine (0.1 mg/ml) in acetone. Fluorescence was read using a Turner filter fluorimeter (excitation 390 nm; emmission 475 nm). Fluorescent standards were prepared using synthetic mixtures of glycine, alanine, and serine in a molar ratio corresponding to the PnF. In all cases the amount of PnF ($Conc_{solution} \times Vol.$) available in the diluted solutions to each piece of polystyrene film was much greater than the amount of PnF ($Conc_{surface} \times Area$) which absorbed to the surface. This ratio is indicated at each data point in Table 14. The means and standard deviations were determined for each data point by conducting multiple assays on 6 to 8 independent samples.

Films were compression molded from polystyrene pellets (Amoco IR3-C0). Disks (7 mm dia.) were punched out using a "one-hole" paper punch. These disks were cleaned and coated with ProNectin®F as described above. The disks were mounted in a 96-well tissue culture plate using our standard methods. One lane of blank wells in the same plate were solution coated with PnF. The cell attachment assay was conducted according to the standard protocol described above.

TABLE 14

Surface Concentration vs. Solution Concentration.

| PnF Solution (µg/ml) | Excess PnF Available | PnF Surface (µg/cm²-PS) | | Cell Attachment Abs @ 595 | |
|---|---|---|---|---|---|
| | | Mean | ± Std Dev | Mean | ± Std Dev |
| 100.00 | 802x | 0.624 | ±0.157 | 0.59 | ±0.06 |
| 10.00 | 140x | 0.479 | ±0.145 | 0.55 | ±0.04 |
| 1.00 | 48x | 0.104 | ±0.087 | n/d | n/d |
| 0.20 | 12.0x | 0.084 | ±0.085 | 0.52 | ±0.02 |
| 0.10 | 8.2x | 0.061 | ±0.066 | 0.29 | ±0.05 |
| 0.02 | 3.2x | 0.031 | ±0.062 | 0.00 | n/d |
| 0.00 | n/a | 0.000 | ±0.077 | | |

The deposition of PnF onto polystyrene surfaces showed a sigmoidal profile of surface concentrations versus solution concentrations which is a characteristic of Langmuirian absorption processes.

At high solution concentrations, the amount deposited onto the surface of the polystyrene reached a plateau. The measured surface concentrations in this plateau region were very close to our estimate of monolayer coverage based on a consideration of the geometry of the ProNectin®F molecule.

Cell attachment activity of the coated polystyrene was remarkably insensitive to coverage of the polystyrene by PnF. Cell attachment reached a plateau at about monolayer coverage of the surface by PnF. Half of the cell attachment activity persisted down to 0.1 monolayer on the specially cleaned polystyrene surfaces. Cell attachment activity did not persist to such low degrees of coverage when PnF was deposited onto a standard commerical grade polystyrene such as Amoco 1R3-C0. The data in Table 14 relating solution concentrations of ProNectin®F to surface deposition and cell attachment performance is essential to designing a commerical coating process.

Stabilization of ProNectin®F

Experiments were conducted using Polystyrene pellets from a lot without added zinc stearate, mineral oil, or wax. The native pellets were ground to a powder in a miniature Waring blender without suspending solvent. The recovered powder was washed with isopropanol on a Buchner funnel, air dried, and sieved to >20 mesh. The ProNectin®F (1.0 mg) was dissolved in 15 ml of formic acid, slurried with 5 g of sieved polystyrene powder, agitated on a vortex mixer, and diluted with 45 ml of deionized water. In another experiment, the ProNectin®F (1.0 mg) and calcium oxide (1.0 mg) was dissolved in the formic acid. In both cases, the recovered polystyrene powder was collected on a Buchner funnel and dried in air without agitation. In one case, the polystyrene powder was compression molded before all residues of formic acid were evaporated. These powders were designated as being coated at 200 ppm ProNectin®F.

Several sample films from each lot of powder were compression molded from 250 mg of coated polystyrene between 304 stainless steel sheets using a Carver press with plattens heated electrically to 150° C. and a maximum force of 1500 kilogmms for 3–5 seconds. Four sample disks for cell attachment assay were taken from the center of each of three films using a standard 7 mm "one-hole-punch". A cell attachment assay was conducted on a single 96-well plate using the standard protocol described above.

TABLE 15

Optical Densities of Cell Attachment Assays Using PnF (200 ppm) On PS

| Comments | | Time [min] | Temp. [°C.] | N | OD [mean] | ±σ | CV |
|---|---|---|---|---|---|---|---|
| Bare Plate | Solution coated with 100 µl of 1 µg/-PnF/ml | | | 5 | 0.761 | ±0.005 | 1% |
| 103,066-C | Std Vortex | ¼ | 150° | 3 | 0.681 | ±0.059 | 9% |
| 103,079-2 | Std Vortex | 5 | 150° | 4 | 0.516 | ±0.055 | 11% |
| 103,079-3 | Formic Residues | ¼ | 150° | 3 | 0.204 | ±0.088 | 43% |
| 103,079-4 | $Ca^{+2}$ | ¼ | 150° | 3 | 0.729 | ±0.040 | 5% |

After the polystyrene disks were mounted on the tissue culture plate with silicone grease dissolved in cyclohexane at 25% w/v, a matrix of optical densities was measured. The optical densities reported in the above table were corrected on a well-by-well basis for the variations in optical densities arising from the "cloudiness" of the inserted polystyrene disks and from the silicone grease used to affix the disks to the bottoms of the wells. Each well thus became its own control. The optical densities were also corrected for the fact that the polystyrene disks tend to pick up a little color during the staining process with the amidoblack.

Occasionally, difficulties were encountered in the cell attachment assays; especially with reduced optical densities for the positive controls. Some of these difficulties might have been a result of contamination by cyclohexane. Cyclohexane is used to apply the silicone grease which serves as an adhesive to affix the polystyrene disks to the bottoms of the wells on the 96-well plate. Removal of the cyclohexane was best achieved using a vacuum oven.

The presence of formic acid residues on samples of polystyrene coated with ProNectin®F, led to reduced O.D.'s upon compression molding compared to fully dried samples. This result is in direct contrast to the result described above in the case of ProNectin®L.

The presence of calcium formate in the coating recipe may have had a protective effect on the ProNectin®F during the compression molding operation.

Lot Reproducibility & Rinses with Calcium Salts

Experiments were conducted using Polystyrene pellets from a lot without added zinc stearate, mineral oil, or wax. The native pellets were ground to a powder in a miniature Waring blender without suspending solvent. The recovered powder was washed with isopropanol on a Buchner funnel, air dried, and sieved to >20 mesh. Samples of ProNectin®F from three separates lots were evaluated for their cell attachment efficacy. The ProNectin®F (1.0 mg) was dissolved in 15 ml of formic acid, slurried with 5 g of sieved polystyrene powder, agitated on a vortex mixer, and diluted with 45 ml of deionized water. The polystyrene powder was recovered by filtration, sucked as dry as possible on the filter, and dried in air. In another experiment, the polystyrene powder was recovered by filtration, rinsed with water, sucked as dry as possible, and dried in air.

In another group of experiments, samples of a single lot of ProNectin®F (1.0 mg) were dissolved in three solvents: 85% formic acid, 6 molar aqueous urea, and 4.5 molar aqueous lithium perchlorate. Coating of the polystyrene powder was conducted as described above. Samples were recovered by filtration, rinsed with 100 mMolar aqueous calcium chloride solutions, sucked as dry as possible on the filter, and dried in air.

Several sample films from each lot of powder were compression molded from 250 mg of coated polystyrene between 304 stainless steel sheets using a Carver press with plattens heated electrically to 150° C. and a maximum force of 1500 kilogmms for 3–5 seconds. Four sample disks for cell attachment assay were taken from the center of each of three films using a standard 7 mm "one-hole-punch". A cell attachment assay was conducted on a single 96-well plate using the standard protocol described above.

TABLE 16

Optical Densities of Cell Attachment Assay

| Comments | | Time [min] | Temp. [°C.] | N | OD [mean] | ±σ | CV |
|---|---|---|---|---|---|---|---|
| Bare Plate | Solution coated with 100 µl of 1 µg/-PnF/ml | | | 8 | 0.491 | ±0.041 | 1% |
| 103,080-C | Lot #26; Formic | ¼ | 150° | 8 | 0.356 | ±0.079 | 27% |
| 103,080-D | Lot #27; Formic | ¼ | 150° | 7 | 0.384 | ±0.079 | 11% |
| 103,066-C | Lot #24; Formic | ¼ | 150° | 8 | 0.374 | ±0.065 | 112% |
| 013,080-H | Lot #26; Formic; Water Rinse | ¼ | 150° | 7 | 0.361 | ±0.132 | 32% |
| 103,080-I | Lot #26; Formic; $CaCl_2$ Rinse | ¼ | 150° | 8 | 0.494 | ±0.043 | 13% |
| 103,080-J | Lot #26; Urea; $CaCl_2$ Rinse | ¼ | 150° | 8 | 0.548 | ±0.036 | 22% |
| 103,080-K | Lot #26; $LiClO_4$; $CaCl_2$ Rinse | ¼ | 150° | 8 | 0.519 | ±0.059 | 15% |

After the polystyrene disks were mounted on the tissue culture plate with silicone grease, a matrix of optical densities was measured. The optical densities reported in the above table were corrected on a well-by-well basis for the variations in optical densities arising from the "cloudiness" of the inserted polystyrene disks and from the silicone grease used to affix the disks to the bottoms of the wells. Each well thus became its own control. The optical densities were also corrected for the fact that the polystyrene disks tend to pick up a little color during the staining process with the amidoblack.

Samples of ProNectin®F from three separate fermentation lots were all functionally equivalent in the cell attachment assay after being coated onto polystyrene powders and compression molded into films.

These data showed that solutions of ProNectin®F made up in 85% formic acid, 6 Molar aqueous urea, and 4.5 Molar aqueous lithium perchlorate were all functionally equivalent when used in the vortex dilution method of coating polystyrene powders.

The ability to substitute 6 m aqueous urea is of great significance to the design and cost of a large scale coating process for polystyrene powders. Avoiding corrosive reagents in the process means that the large scale process equipement can be made of less expensive materials of construction.

Calcium Stabilization of ProNectin®F

Experiments were conducted using polystyrene (PS) pellets from a lot without added zinc stearate, mineral oil, or wax. The native pellets were ground to a powder in a miniature Waring blender without suspending solvent. The recovered powder was washed with isopropanol on a Buchner funnel, air dried, and sieved to >20 mesh. ProNectin®F (8.0 mg) was dissolved in 8 ml of formic acid and added to 400 ml of 150 mM NaCl solution contained in a 1000 ml Erlenmeyer flask fitted with a magnetic stirrer to yield a final concentration of 20 µg-PnF/ml. The polystyrene powders were prewetted with mixtures of methanol by immersing the PS in the methanol and applying house vacuum to the head space. Excess methanol was decanted from the wetted PS powders before the PS powders were added to the diluted solution of PnF. The slurry was stirred for 2 hours at room temperature before being filtered. One sample of powder was rinsed with water, the sample of PS powder was resuspended in 100 mMolar calcium chloride solution, which was adjusted to pH 7, stirred for 10 minutes, and filtered. Theses samples of PS powder were then resuspended in 10 mMolar calcium chloride solution, which was adjusted to pH 7, stirred for 10 minutes, filtered, sucked as dry as possible and dried in air. A sample (2.0 g) of polystyrene powder coated with ProNectin®F was placed into a Pyrex glass tube (16 mm×100 mm); sealed with a rubber septum cap, sparged with nitrogen, and heated in a thermostatted oil bath preheated to 200° C. for 5 minutes.

sities was measured. The optical densities reported in the above table were corrected on a well-by-well basis for the variations in optical densities arising from the "cloudiness" of the inserted polystyrene disks and from the silicone grease used to affix the disks to the bottoms of the wells. Each well thus became its own control. The optical densities were also corrected for the fact that the polystyrene disks tend to pick up a little color during the staining process with the amidoblack.

ProNectin®F can be stabilized towards thermally induced deactivation. Rinsing the coated PS powders with calcium chloride solution produce samples which retained much more activity than the standard samples after a thermal challenge of 5 minutes at 200°C.

The coating methodology used in preparing these samples is important because it can be scaled for working with larger lots of polystyrene powder. The engineering aspects of working with stirred slurries of powders is well understood and is scaleable to larger sizes in a straightforward manner. The "tool", the coating technique, now exists which makes it possible to work with multi-kilogrmm lots of polystyrene powders. Prewetting the polystyrene with methanol was conducted in order to improve the contact between the aqueous solution of PnF and the hydrophobic surface of the polystyrene powders. No attempt was made to exchange the methanol with water before coating. Such a prewetting was clearly counterindicated by the data in this table. Coating of dry polystyrene powders performed better. The effect was more apparent in those samples which were "stressed" at high temperatures.

Thermal Stress Matrix for Calcium Stabilized ProNectin®F

Experiments were conducted using Polystyrene pellets from a lot without added zinc stearate, mineral oil, or wax. The native pellets were ground to a powder in a miniature Waring blender without suspending solvent. The recovered

TABLE 17

Optical Densities of Cell Attachment Assays

| | Comments | Time [min] | Temp. [°C.] | N | OD [mean] | ±σ | CV |
|---|---|---|---|---|---|---|---|
| Bare Plate | Solution coated with 100 µl of 1 µg/-PnF/ml | | | 8 | 0.549 | ±0.044 | 1% |
| 103,081-1A | Wetted 100% MeOH | ¼ | 150° | 8 | 0.531 | ±0.094 | 18% |
| 103,081-1B | Wetted 100% MeOH | 5 | 200° | 8 | 0.135 | ±0.066 | 49% |
| 103,081-2B | Wetted 100% MeOH; Ca$^{+2}$ | 5 | 200° | 7 | 0.194 | ±0.052 | 27% |
| 103,081-3A | Wetted 50% MeOH | ¼ | 150° | 8 | 0.560 | ±0.062 | 11% |
| 103,081-3B | Wetted 50% MeOH | 5 | 200° | 8 | 0.065 | ±0.073 | 112% |
| 103,081-4A | Wetted 50% MeOH; Ca$^{+2}$ | ¼ | 150° | 8 | 0.554 | ±0.079 | 14% |
| 103,081-4B | Wetted 50% MeOH; Ca$^{+2}$ | 5 | 200° | 7 | 0.311 | ±0.099 | 32% |
| 103,081-5A | Dry Powder | ¼ | 150° | 8 | 0.519 | ±0.065 | 13% |
| 103,081-5B | Dry Powder | 5 | 200° | 8 | 0.172 | ±0.037 | 22% |
| 103,081-6A | Dry Powder; Ca$^{+2}$ | ¼ | 150° | 8 | 0.581 | ±0.050 | 9% |
| 103,081-6B | Dry Powder; Ca$^{+2}$ | 5 | 200° | 8 | 0.418 | ±0.064 | 15% |

Several sample films from each lot of powder were compression molded from 250 mg of coated polystyrene between 304 stainless steel sheets using a Carver press with plattens heated electrically to 150° C. and a maximum force of 1500 kilogrmms for 3–5 seconds. Four sample disks for cell attachment assay were taken from the center of each of three films using a standard 7 mm "one-hole-punch". A cell attachment assay was conducted on a single 96-well plate using the standard protocol described above.

After the polystyrene disks were mounted on the tissue culture plate with silicone grease, a matrix of optical denpowder was washed with isopropanol on a Buchner funnel, air dried, and sieved to >20 mesh. ProNectin®F (8.0 mg) was dissolved in 8 ml of 10 molar aqueous urea and diluted into 400 ml of 150 mmolar aqueous sodium chloride solution contained in a 1000 ml Erlenmeyer flask. Polystyrene powder (20 g) was added as a dry powder, and was stirred for 1 hour at room temperature. The recovered polystyrene powder was collected on a Buchner funnel, washed with 100 mM calcium chloride solution, washed with 10 mM calcium chloride solution, sucked as dry as possible, and dried in air without agitation. The loading of ProNectin®F onto this polystyrene powder was estimated from previous measurements of the surface area of the powder and the adsorption isotherm.

A sample (2.0 g) of polystyrene powder coated with ProNectin®F (200 ppm) was placed into a Pyrex glass tube (16 mm×100 mm); sealed with a rubber septum cap, sparged with nitrogen, and heated in a thermostatted oil bath preheated to the required temperature for varying lengths of time. Several sample films from each lot of powder were compression molded from 250 mg of coated polystyrene between 304 stainless steel sheets using a Carver press with plattens heated electrically to 150° C. and a maximum force of 1500 kilogmms for 3–5 seconds. Four sample disks for cell attachment assay were taken from the center of each of three films using a standard 7 mm "one-hole-punch". A cell attachment assay was conducted on a single 96-well plate using the standard protocol described above.

TABLE 18

Optical Densities of Cell Attachment Assays

| | PnF [ppm] | Time [min] | Temp. [°C.] | N | OD [mean] | ±σ | CV |
|---|---|---|---|---|---|---|---|
| Bare Plate | Solution coated with 100 µl of 1 µg/-PnF/ml | | | 8 | 0.690 | ±0.050 | 7% |
| 103,082-A | 20 | ¼ | 150° | 8 | 0.691 | ±0.035 | 5% |
| 103,082-B | 20 | 5 | 150° | 7 | 0.610 | ±0.083 | 14% |
| 103,082-C | 20 | 40 | 150° | 7 | 0.554 | ±0.038 | 7% |
| 103,082-D | 20 | 10 | 165° | 7 | 0.561 | ±0.064 | 11% |
| 103,082-E | 20 | 5 | 180° | 7 | 0.517 | ±0.070 | 14% |
| 103,082-F | 20 | 20 | 180° | 5 | 0.330 | ±0.143 | 43% |
| 103,082-G | 20 | 10 | 195° | 7 | 0.364 | ±0.118 | 32% |
| 103,082-H | 20 | 40 | 195° | 8 | 0.204 | ±0.072 | 35% |
| 103,082-I | 20 | 5 | 210° | 6 | 0.348 | ±0.080 | 23% |
| 103,082-J | 20 | 10 | 210° | 6 | 0.205 | ±0.077 | 36% |
| 103,082-K | 20 | 20 | 210° | 8 | 0.106 | ±0.079 | 75% |

After the polystyrene disks were mounted on the tissue culture plate with silicone grease, a matrix of optical densities was measured. The optical densities reported in the above table were corrected on a well-by-well basis for the variations in optical densities arising from the "cloudiness" of the inserted polystyrene disks and from the silicone grease used to affix the disks to the bottoms of the wells. Each well thus became its own control. The optical densities were also corrected for the fact that the polystyrene disks tend to pick up a little color during the staining process with the amidoblack.

The performance of the compression molded disks of polystyrene in the cell attachment assay decreased with increasing time and with increasing temperature in a complex manner. These data confirmed that ion exchange of ProNectin®F on the surface of the polystyrene powder with calcium ions conferred stabilization towards thermal deactivation during the thermal challenge.

The time-temperature experiments represented a response surface which was fitted by multi-variate regression analysis. A model was defined which assumed a semi-first order reaction for thermal degradation with the rate constant being exponential in temperature. The fit of this second equation was $R^2=0.969$, and had the satisfying property of fitting only three adjustable parameters to the 11 data points. The following parameters added together to form an equation which can be used to interpolate between points on the time-temperature response surface.

Pammeter estimates for $Ln[Ln(A_0/A)] R^2=0.969$ Calcium stabilized.

| Term | Coefficient | Std Error | t Ratio | Prob > |t| |
|---|---|---|---|---|
| Intercept | 11.878449 | 1.22902 | 9.66 | 0.0000 |
| Ln t | 0.3219709 | 0.04650 | 6.92 | 0.0001 |
| 1/°K. | −6009.332 | 539.389 | −11.14 | 0.0000 |

Preferred Embodiments of Coating Process.

The objective of most of the experimentation described herein has been to make a mixture of polystyrene and ProNectin®F and fabricate it into plastic ware useful in tissue culture applications. The fabrication method to be used is injection molding. The injection molding process is characterized by parameters of time, temperature, and mechanical shear stress; all of which determine the activity of the ProNectin®F at the end of the fabrication process.

Compression molding may be used as a general method for fabricating plastics into sheets. Compression molding is easier to carry out on a laboratory scale than injection molding. Compression molding combined with the thermal stress experiments was used to model the time and temperature parameters of the injection molding process. The mechanical shear stress parameter can not be readily modeled anywhere except in an actual injection molding experiment.

Compression molding experiments were used to determine how best to mix ProNectin®F with polystyrene. The performance of the best candidate mixture was validated for tolerance to shear stress in an actual injection molding experiment described below.

Grade of Polystyrene

The preferred embodiment uses a grade of polystyrene which contains no mold release agents, lubricants, or viscosity modifiers. Amoco is a major manufacturer of polystyrene. The IR3-C0 grade contains no additives. The GR3-C7 grade contains a mix of additives which are commonly specified for injection molding applications. The detrimental effects of the presence of such additives is shown in the section entitled "Effects of Additives in the Polystyrene", and is summarized below:

TABLE 19

Effect of Additives in the Polystyrene.

| Sample | PnF [ppm] | Polymer Disks | N | OD [mean] | ±σ | CV |
|---|---|---|---|---|---|---|
| Bare Plate | | Solution coated 1 µg-PnF/ml | 8 | 0.797 | ±0.037 | 5% |
| 102,028-2 | 200 | PS [Amoco IR3-C0] | 8 | 0.557 | ±0.046 | 8% |
| 102,028-10 | 200 | PS [Amoco GR3-C7] | 8 | 0.106 | ±0.117 | 111% |

Particle Size Of Polystyrene

ProNectin®F will attach to the exposed surface of polystyrene particles. The goal is to achieve an appropriate ratio of µg-PnF per g-PS. One parameter which defines the absolute amount of ProNectin®F which attaches to the polystyrene is the surface area of the polystyrene particles. Small particles possess a greater surface to volume ratio. In general, the use of smaller particles favors absorbing more ProNectin®F per gram of polystyrene. However, it is more difficult to make smaller particles. The preferred embodiment uses polystyrene ground to pass a 20 mesh sieve (>20 mesh). This choice is supported by the relative insensitivity of performance to mesh size over the range of 20 mesh to >100 mesh as shown in the section entitled "Effect of Deposition Methods and Mesh Size', and is summarized below:

TABLE 20

Effect of Deposition Method & Mesh Size

| Sample | PnF [ppm] | Deposition Method | PS Powder mesh range | N | OD [mean] | ±σ | CV |
|---|---|---|---|---|---|---|---|
| Bare Plate | | Solution coated with 100 μl of 1 μg-PnF/ml | | 8 | 0.655 | ±0.099 | 15% |
| 103,065-C | 150 | Vortex Dil'n | >100 | 8 | 0.468 | ±0.112 | 24% |
| 103,065-F | 150 | Vortex Dil'n | 60–80 | 8 | 0.532 | ±0.071 | 13% |
| 103,065-I | 150 | vortex Dil'n | 20–40 | 8 | 0.410 | ±0.043 | 10% |

Coating Methods

Evaporative Deposition

In evaporative deposition, a fixed amount of ProNectin®F is dissolved in formic acid solvent, polystyrene powder is added to the solvent, and the solvent is evaporated. All of the ProNectin®F is presumed to be deposited onto the polystyrene powder. A plot of cell attachment activity versus ProNectin®F concentration showed a plateau above 400 ppm. The results are shown in the section entitled "Deposition of ProNectin®F onto Polystyrene by Evaporative Coating", and is summarized below:

TABLE 21

Deposition of ProNectin ® F onto Polystyrene by Evaporative Coating.

| | PnF [ppm] | PS Powder mesh range | N | OD [mean] | ±σ | CV |
|---|---|---|---|---|---|---|
| Bare Plate | Solution coated with 100 μl of 1 μg/-PnF/ml | | 8 | 0.573 | ±0.024 | 4% |
| 102-17-03 | 400 | >100 | 8 | 0.493 | ±0.069 | 14% |
| 103-64-A | 400 | >100 | 8 | 0.461 | ±0.045 | 10% |
| 103-64-B | 200 | >100 | 8 | 0.352 | ±0.086 | 24% |
| 103-64-C | 150 | >100 | 8 | 0.181 | ±0.055 | 30% |
| 103-64-D | 100 | >100 | 8 | 0.115 | ±0.056 | 49% |
| 103-64-E | 50 | >100 | 8 | 0.012 | ±0.049 | 408% |

Coating Methods

Vortex Deposition

In vortex deposition, a fixed amount of ProNectin®F is dissolved in formic acid solvent, polystyrene powder is added to the solvent, and a non-solvent is added under conditions of vigorous agitation (vortexing). ProNectin®F is deposited onto the polystyrene powder. Under some circumstances, this method may be the preferred embodiment because this method achieved high attachment activities using relatively smaller amounts of ProNectin®F in the coating mixture. A plot of cell attachment activity versus ProNectin®F concentration showed a plateau above 100 ppm. The results are shown in the section entitled "Deposition of ProNectin®F onto Polystyrene by Vortex Dilution Coating", and is summarized below:

TABLE 22

Deposition of ProNectin ® F onto Polystyrene by Vortex Dilution Coating.

| | PnF [ppm] | PS Powder mesh range | N | OD [mean] | ±σ | CV |
|---|---|---|---|---|---|---|
| Bare Plate | Solution coated with 100 μl of 1 μg/-PnF/ml | | 8 | 0.799 | ±0.026 | 3% |
| 103-66-00 | Solution coated with 100 μl of 1 μg/-PnF/ml | | 8 | 0.747 | ±0.052 | 7% |
| 103-66-A | 300 | >20 | 8 | 0.516 | ±0.048 | 9% |
| 103-66-B | 250 | >20 | 8 | 0.641 | ±0.073 | 11% |
| 103-66-C | 200 | >20 | 8 | 0.627 | ±0.068 | 11% |
| 103-66-D | 150 | >20 | 8 | 0.650 | ±0.057 | 9% |
| 103-66-E | 100 | >20 | 8 | 0.544 | ±0.067 | 12% |
| 103-66-F | 50 | >20 | 8 | 0.592 | ±0.060 | 10% |

Vortex deposition may be conducted using ProNectin®F dissolved in 85% formic acid, 10.0 molar aqueous urea, or 4.5 molar aqueous lithium perchlorate. Dissolution in aqueous urea is the preferred embodiment in the case of vortex dilution because urea is the least toxic or corrosive reagent of this group. These results are shown in the section entitled "Lot Reproductibility & Rinses with Calcium Salts", and are summarized below:

TABLE 23

Lot Reproducibilities and Rinses with Calcium Salts.

| | Comments | Time [min] | Temp [°C.] | N | OD [mean] | ±σ | CV |
|---|---|---|---|---|---|---|---|
| Bare Plate | Solution coated with 100 μl of 1 μg/-PnF/ml | | | 8 | 0.491 | ±0.041 | 1% |
| 103,080-H | Lot #26; Formic; Water Rinse | ¼ | 150° | 7 | 0.361 | ±0.132 | 32% |
| 103,080-I | Lot #26; Formic; CaCl$_2$ Rinse | ¼ | 150° | 8 | 0.494 | ±0.043 | 13% |
| 103,080-J | Lot #26; Urea; CaCl$_2$ Rinse | ¼ | 150° | 8 | 0.548 | ±0.036 | 22% |
| 103,080-K | Lot #26; LiClO$_4$; CaCl$_2$ Rinse | ¼ | 150° | 8 | 0.519 | ±0.059 | 15% |

This list of solvent systems is not exhaustive. Other chaotropic reagents may be used to dissolve ProNectin®F in aqueous solutions. Other organic liquids may be used to dissolve the ProNectin®F. Other organic liquids may be used as non-solvents.

Coating Methods
Stirred Deposition

In stirred deposition, ProNectin®F is initially dissolved at "high" concentration (~1 mg/ml) in a suitable solvent. Preferred solvent is 10.0 molar urea. A working solution for coating is prepared by diluting the concentrate down to 5–50 µg/ml into 150 mmolar aqueous sodium chloride solution. Coating of the polystyrene is conducted by adding the powdered polystyrene to the working solution and stirring for 1 hour. Three variants were used, which differed in the way the polystyrene powder was prewetted before being added to the working solution. These results are shown in the section entitled "Calcium Stabilization of ProNectin®F", and are summarized below:

The preferred embodiment is to work at concentrations in the range of 5–50 µg-PnF/ml. The most preferred embodiment is to work at 10–20 µg-PnF/ml. Other concentrations may become preferred for reasons relating coating costs to the cell attachment performance of the final plastic ware products.

Using the techniques for the Fluorescamine assay described above, the ProNectin®F actually deposited onto polystyrene powders was quantitated. Preparation of compression molded film samples and a cell attachment assay were conducted using standard protocols described above. The results of the assay are shown in table 25.

TABLE 24

Calcium Stabilization of ProNectin ® F.

| | Comments | Time [min] | Temp. [°C.] | N | OD [mean] | ±σ | CV |
|---|---|---|---|---|---|---|---|
| Bare Plate | Solution coated with 100 µl of 1 µg/-PnF/ml | | | 8 | 0.549 | ±0.044 | 1% |
| 103,081-5A | Dry Powder | ¼ | 150° | 8 | 0.519 | ±0.065 | 13% |
| 103,081-3A | Wetted 50% MeOH | ¼ | 150° | 8 | 0.560 | ±0.062 | 11% |
| 103,081-1A | Wetted 100% MeOH | ¼ | 150° | 8 | 0.531 | ±0.094 | 18% |
| 103,081-5B | Dry Powder | 5 | 200° | 8 | 0.172 | ±0.037 | 22% |
| 103,081-6B | Dry Powder; Ca$^{+2}$ | 5 | 200° | 8 | 0.418 | ±0.064 | 15% |
| 103,081-4B | Wetted 50% MeOH; Ca$^{+2}$ | 5 | 200° | 7 | 0.311 | ±0.099 | 32% |
| 103,081-2B | Wetted 100% MeOH; Ca$^{+2}$ | 5 | 200° | 7 | 0.194 | ±0.052 | 27% |

TABLE 25

Stirred Deposition of ProNectin ® F onto Polystyrene Powders.

| | PnF [µg/ml] Solution | PnF [µg/cm$^2$] Surface | Time [min] | Temp. [°C.] | N | OD [mean] | ±σ | CV |
|---|---|---|---|---|---|---|---|---|
| Bare Plate | Solution coated with 100 µl of 1 µg/-PnF/ml | | | | 8 | 0.627 | ±0.014 | 2% |
| 103-083-A1 | 40 | 35.6 | ¼ | 150° | 8 | 0.615 | ±0.019 | 3% |
| 103-083-B1 | 20 | 26.1 | ¼ | 150° | 8 | 0.599 | ±0.040 | 7% |
| 103-083-C1 | 10 | n/d | ¼ | 150° | 8 | 0.602 | ±0.021 | 3% |
| 103-683-D1 | 5 | 18.6 | ¼ | 150° | 8 | 0.531 | ±0.039 | 7% |

Based on the results from compression moldings, the preferred embodiment is to use the dry polystyrene powder because this method is easiest to do. The rational for using dry powder becomes much more compelling when the results from thermal stress and calcium stabilization are considered. In these cases, preparations made using dry powdered polystyrene provided superior performance.

Of the three methods for depositing ProNectin®F onto polystyrene powders, the stirred deposition method is the preferred embodiment. It is the most readily scaled to handling larger quantities of polystyrene.

During the process of stirred deposition, the concentration of ProNectin®F in the working solution determines the amount deposited onto the surface of the polystyrene powder. In order to characterize this deposition phenomenon, we measured the deposition of ProNectin®F onto flat sheets of polystyrene with known surface areas. These results are shown in the section entitled "Relationship of Solution Concentrations to Surface Deposition".

Based on these results, the preferred embodiment is to coat polystyrene from a solution concentration of 10–20 µg/ml.

Stabilized ProNectin®F

The results of thermal stress experiments are shown in the section entitled "Thermal Stress Matrix for Unstabilized ProNectin®F". The first indication that it is possible to intervene in the thermal deactivation process was observed in the experiments shown in the section entitled "Lot Reproducibility & Rinses with Calcium Salts", as summarized below:

TABLE 26

Lot Reproducibilities & Rinses with Calcium Salts.

| | Comments | Time [min] | Temp [°C.] | N | OD [mean] | ±σ | CV |
|---|---|---|---|---|---|---|---|
| Bare Plate | Solution coated with 100 μl of 1 μg/-PnF/ml | | | 8 | 0.491 | ±0.041 | 1% |
| 103,080-H | Lot #26; Formic; Water Rinse | ¼ | 150° | 7 | 0.361 | ±0.132 | 32% |
| 103,080-I | Lot #26; Formic CaCl₂ Rinse | ¼ | 150° | 8 | 0.494 | ±0.043 | 13% |

In this experiment, no thermal stress other than that resulting from the compression molding was encountered. The sample which was rinsed with calcium chloride solution performed significantly better than the sample rinsed with water.

The first demonstration that it was possible to intervene in the thermal deactivation process under more severe conditions was observed in the experiments shown in the section entitled "Calcium Stabilization of ProNectin®F", as summarized below:

TABLE 27

Calcium Stabilization of ProNectin ® F.

| | Comments | Time [min] | Temp. [°C.] | N | OD [mean] | ±σ | CV |
|---|---|---|---|---|---|---|---|
| Bare Plate | Solutuion coated with 100 μl of 1 μg/-PnF/ml | | | 8 | 0.549 | ±0.044 | 1% |
| 103,081-5B | Dry Powder | 5 | 200° | 8 | 0.172 | ±0.037 | 22% |
| 103,081-6B | Dry Powder; Ca⁺² Rinse | 5 | 200° | 8 | 0.418 | ±0.064 | 15% |

The calcium chloride solutions were prepared from calcium chloride desiccant which contained titratable base in the amount of 0.006 meq/g. The presence of the titratable base led to slightly elevated pH's. The preferred embodiment is to conduct the rinse with calcium chloride solution in two stages: 100 mMolar $CaCl_2$ followed by 10 mMolar $CaCl_2$, although in some cases, 1 mmolar $CaSO_4$ may be substituted for the 10 mmolar $CaCl_2$ or may be used alone.

The extent to which ProNectin®F may be stabilized towards thermal deactivation is shown in the section entitled "Thermal Stress Matrix for Calcium Stabilized ProNectin®F".

The data points in Table 18 were subjected to multivariate regression analysis, and a equation was derived for predicting deactivation as a function of time and temperature. The general form of this equation was a semi-first order decay with the rate constant exponential in temperature.

The effects of calcium stabilization are apparent when compared against the data in Table 13. Comparing the fitting equations for the calcium stabilized and the non-stabilized cases was instructive. The coefficient on the 1/K° term was interpretable as the energy, $E_a/R$, of the thermal decomposition reaction, with $E_a$, =−12 Kcal/mole. Surprisingly, this activation energy does not change, within the confidence intervals, between the two response surfaces. What does change was a decrease in the pre-exponential frequency term $Ln|A|$.

The coefficient on the term in time also changes. The interpretation of this last effect was not clear. It may be related to a surface diffusion phenomenon. In any case, the equations which predict cell culture performance as a function of time and temperature during the thermal challenge are of the form:

$$Ln\left\{ Ln\left(\frac{I_0}{I}\right) \right\} = Ln(A) + b*Ln(t) + \frac{E_a}{RT}$$

$$Ln\left[\frac{I}{I_0}\right] = -A*(e^{-\frac{E_a}{RT}})*t^b$$

$$\frac{I}{I_0} = e^{-A*(e^{-\frac{E_a}{RT}})*t^b}$$

Where the coefficients have the values:

| | Calcium Stabilized | | Non-Stabilized | |
|---|---|---|---|---|
| Terms | Coefficient | Std Error | Coefficient | Std Error |
| Ln[A] | 11.8784 | ±1.2290 | 12.2560 | ±1.4924 |
| b | 0.32197 | ±0.04650 | 0.70493 | ±0.08461 |
| $E_a$ | −11,933 | ±1070 | −12,767 | ±1337 |
| $R^2$ | 0.969 | | 0.963 | |

The significance of calcium stabilization is that we now have a larger time-temperature window through which to conduct the thermomolding operation. The requirements for the time-temperature window are defined by the characteristics of the thermomolding process itself. For instance, in the case of injection molding, time is defined by the ratio between the contained volumes within the heated barrel of the screw extruder and within the mold, and by the cycle time on the mold, while temperature in defined by the nature of the plastic and the complexity of the mold. Together, these process parameters define "how long" and "how hot" the polypeptide will be stressed.

The preferred embodiment is to ion exchange the ProNectin®F on the surface of the polystyrene with calcium ion at slightly elevated pH, pH 8.6. Other combinations of multivalent metal cations and pH may serve to confer thermal stabilization. Calcium was chosen because it is commonly found in tissue culture media. A small increment of calcium leaching into the tissue culture media from the plastic ware activated with ProNectin®F would constitute only a minimum perturbation on the function of the tissue culture media. Other metal ions which might be useful for stabilization are zinc and magnesium. Trivalent ions such as aluminum may also be useful.

Shear Stress Testing

Native polystyrene pellets (Amoco IR3-P0) were ground to a powder using an 8" vertical grinder and screened to a nominal size of >35 mesh with oversize particles being returned for regrinding. The measured mesh size distribution which was obtained is: (mesh,wt %)<30, 0.2%; 30–35, 11.3%; 35–40, 15.9%; 40–60, 44.9%; 60–80, 18.4%; 80–100, 5.9%; & >100, 3.4%. The polystyrene powder (2000 g) was slurried in 3500 ml of isopropanol for 5 minutes, filtered on a Buchner funnel, washed on the filter with an additional 2000 ml of isopropanol, sucked as dry as possible, and dried in air under ambient conditions.

ProNectin®F (500 mg) was dissolved in 500 ml of 10.0 molar aqueous urea solution to yield the stock solution of 1 mg/ml concentration. Aqueous saline (150 mmolar) was prepared by dissolving by sodium chloride (86.5 g) in 10.0 liters of deionized water. The saline solution was agitated using a mechanical stirrer (Lightning model L1UO8P) set at 1025 rpm, the power at 5.8 watts, and the pumping capacity at 365 L/min., with an impeller (model A-310) at the end of the shaft which was angled at 65° to the surface of the solution. Stock ProNectin®F solution (100 ml) was added dropwise over about 3 minutes to the stirred saline to give a final concentration of ProNectin®F of 10 µg/ml. To this solution was added 500 g of the ground, washed and dried polystyrene powder >35 mesh. The slurry was allowed to stir for 1 hour at ambient temperature. The polystyrene powder was recovered using a 26 cm Buchner funnel with a stationary porous filter (70 microns). After being sucked as dry as possible, the polystyrene powder was slurried on the funnel with 2 L of 1 mmolar calcium sulfate solution and again sucked dry. This treatment was repeated twice more. During the final filtration, the filter cake was compacted under an elastic dam. The recovered polystyrene powder was spread into a layer about 3 cm deep and dried for 15 hours in a forced draft oven at 40° C. This oven dried polystyrene powder (750 g) was loaded into a 2000 ml lyophilizer tube, connected to a vacuum line fitted with a trap cooled in liquid nitrogen, and evacuated to 0.008 Torr at 25° C. for 1 hour to achieve final drying. The vacuum line was back filled with dry nitrogen to ambient pressure. The lyophilizer tube was removed from the vacuum line, and its access port was sealed with a rubber stopper. The vacuum dried polystyrene powder was stored in these tubes until being poured into the feed hopper of the injection molding machine.

Injection molding using a 1.5 Kg sample of the polystyrene prepared above was conducted using a 5 ounce (141.8 g) TMC injection molding machine. The injection molding was conducted on a cycle time of 25 seconds. The mold used in this test was fashioned in a block of P20 semi-hardened tool steel with a disk shaped cavity of dimensions 1.188" diameter×0.060" thickness using a 15° draft angle. The gate between the runner and the cavity was designed to exacerbate shear stress effects and had dimensions of 0.040"× 0.060"×0.030" (height×width×length). A second mold cavity of completely arbitrary design was installed in the mold frame to increase the shot size to 61.5 grams so that the residence time in the barrel was approximately 58 seconds. The temperature profile on the barrel was: nozzle, 375° F.; front, 359° F.; middle, 360° F., and rear, 347°F.

Disks prepared in this manner from the coated polystyrene powder were optically indistinguishable from disks prepared from native polystyrene pellets (Amoco IR3-C0) as judged by the transparency of the disk portion of the mold. The sensitivity of the ProNectin®F to shear stresses inherent in the injection molding process was judged by regrinding samples of the molded objects and compression molding the reground polystyrene powder into films suitable for inclusion in the cell attachment assay described above. Shear stress is concentrated at the gate to the mold cavity. To judge this effect, samples for regrinding were taken from the runner immediately before the gate to the disk shaped cavity and from the disk shaped cavity. The results of these cell attachment 25 assays are presented in Table 28.

TABLE 28

| Shear Stress Testing During Injection Molding | | | | | | | |
|---|---|---|---|---|---|---|---|
| | PnF [ppm] | Time | Temp | N | OD [mean] | ±σ | CV |
| Bare Plate | Solution coated with 100 µl of 1 µg-PnF/ml | | | 8 | 0.396 | ±0.064 | 16% |
| 103,092-Z | 20 | 0.25 | 150° C. | 8 | 0.385 | ±0.059 | 13% |
| Reground Runner | 20 | 1.0 | 193° C. | 8 | 0.234 | ±0.075 | 32% |
| Reground Disk | 20 | 1.0 | 193° C. | 8 | 0.059 | ±0.027 | 46% |

The coated powder (103,092-Z) when compression molded in the form of a thin sheet performed equivalent to the solution coated bare plate in the cell attachment assay. The polystyrene which was recovered after the injection molding also showed activity in the cell attachment assay. Passage of the molten mixture of ProNectin®F and polystyrene through the gate into the disk shaped cavity led to a deterioration in cell attachment activity compared to the activity of the sample reground from the section of the runner immediately before the gate. This implicates shear stress as a mechanism for deactivating the ProNectin®F during the injection molding process. Shear stress can be alleviated through the design of the sprues, runners, gates, and cavities of the mold. The result of this experiment showed that ProNectin®F can undergo both thermal and mechanical stresses inherent in the injection molding process and retain its cell attachment function.

The compositions and methods disclosed herein reduce the need for solution coating of finished plastic surfaces. The inventions offer substantial improvement over previously used methods for providing surfaces activated with polypeptides by allowing any molded device to be activated with one or more thermostable polypeptides simultaneous with the thermomolding process. This single step reduces costs associated with secondary manufacturing processes for deposition of polypeptides on the surface of thermomolded articles, many of which are solvent based, and provides the ability to produce finished goods at lower unit cost than conventional methods allow. Furthermore, the disclosed compositions and methods provide for the incorporation of thermostable polypeptides into devices whose shapes (e.g. spherical or otherwise three-dimensional) are not readily amenable to solution coating processes.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A composition comprising a biologically functional thermostable polypeptide interdispersed with a thermoplastic resulting from a melt at a temperature of at least 60° C., wherein said polypeptide is at least about 25 kD, has repeating units from elastin, collagen, keratin or silk proteins, and sequences intervening said repeating units, said intervening sequences having chemically active amino acids or a naturally occurring sequence having binding specificity for a protein receptor.

2. The composition of claim 1, wherein said intervening sequence is from 3 to about 60 amino acids in length.

3. The composition of claim 1, wherein said polypeptide has a molecular weight of at least 50 kD.

4. The composition of claim 1, wherein said intervening sequence comprises RGD.

5. The composition of claim 4 wherein said protein polymer is ProNectin®F (SLPF) or SLPL3.0.

6. The composition of claim 1 wherein said thermoplastic is polystyrene, polyethylene, polypropylene, or polymethylmethacrylate.

7. The composition of claim 1 further comprising a polypeptide thermostability enhancing additive.

8. A formed object produced by contacting a plastic with a biologically functional thermostable polypeptide, heating said plastic and polypeptide to at least 60° C. for at least 15 seconds to create a melt, molding said melt to form a biologically functional thermostable polypeptide interdispersed within a thermoplastic, wherein said polypeptide is at least about 25 kD, has repeating units from elastin, collagen, keratin or silk proteins, and sequences intervening said repeating units, said intervening sequences having chemically active amino acids or a naturally occurring sequence having binding specificity for a protein receptor.

9. A method for producing a biologically functional thermostable polypeptide interdispersed within a thermoplastic, said method comprising:

forming a mixture of plastic and said thermostable polypeptide, heating said thermoplastic and said polypeptide to create a melt, molding said melt into a predetermined form, whereby a biologically functional thermostable polypeptide is interdispersed within a thermoplastic, wherein said polypeptide is at least about 25 kD, has repeating units from elastin, collagen, keratin or silk proteins, and sequences intervening said repeating units, said intervening sequences having chemically active amino acids or a naturally occurring sequence having binding specificity for a protein receptor.

10. A method for producing biologically functional ProNectin®F (SLPF) interdispersed within a thermoplastic; said method comprising:

forming a mixture of a thermoplastic and ProNectin®F (SLPF), heating said thermoplastic and said ProNectin®F (SLPF) to create a melt, molding said melt into a predetermined form, whereby biologically functional ProNectin®F (SLPF) is interdispersed within said thermoplastic.

* * * * *

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
    ( A ) LENGTH: 44 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:1:

```
Lys  Lys  Met  Gly  Ala  Gly  Ala  Gly  Ser  Gly  Ala  Gly  Ala  Gly  Ser  Gly
 1              5                        10                       15

Ala  Ala  Val  Thr  Gly  Arg  Gly  Asp  Ser  Pro  Ala  Ser  Ala  Ala  Gly  Tyr
              20                       25                       30

Gly  Ala  Gly  Ala  Gly  Ser  Gly  Ala  Gly  Ala  Gly  Ser
              35                       40
```

( 2 ) INFORMATION FOR SEQ ID NO:2:

( i ) SEQUENCE CHARACTERISTICS:
    ( A ) LENGTH: 45 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:2:

CGCTACGTAG TTCTGCCACG TCCGGTATGT TTCGAAAAAG CTGCA     45

( 2 ) INFORMATION FOR SEQ ID NO:3:

( i ) SEQUENCE CHARACTERISTICS:
    ( A ) LENGTH: 45 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:3:

GCTTTTTCGA AACATACCGG ACGTGGCAGA ACTACGTAGC GTGCA     45

( 2 ) INFORMATION FOR SEQ ID NO:4:

( i ) SEQUENCE CHARACTERISTICS:
    ( A ) LENGTH: 222 base pairs
    ( B ) TYPE: nucleic acid
    ( C ) STRANDEDNESS: double
    ( D ) TOPOLOGY: linear ( i i ) MOLECULE TYPE: cDNA ( i x ) FEATURE:
    ( A ) NAME/KEY: CDS
    ( B ) LOCATION: 1..222

( x i ) SEQUENCE DESCRIPTION: SEQ ID NO:4:

```
GGT  GCC  GGC  AGC  GGT  GCA  GGA  GCC  GGT  TCT  GGA  GCT  GGC  GCG  GGC  TCT     48
Gly  Ala  Gly  Ser  Gly  Ala  Gly  Ala  Gly  Ser  Gly  Ala  Gly  Ala  Gly  Ser
 1              5                        10                       15
```

| | | | | | | | | | | | | | | | | |
|---|---|---|---|---|---|---|---|---|---|---|---|---|---|---|---|---|
| GGC | GCG | GGC | GCA | GGA | TCC | GGC | GCA | GGC | GCT | GGT | TCT | GGC | GCA | GGG | GCA | 96 |
| Gly | Ala | Gly | Ala | Gly | Ser | Gly | Ala | Gly | Ala | Gly | Ser | Gly | Ala | Gly | Ala | |
| | | | 20 | | | | | 25 | | | | | 30 | | | |
| GGC | TCT | GGC | GCA | GGA | GCG | GGG | TCT | GGA | GCT | GCA | CGC | TAC | GTA | GTT | CTG | 144 |
| Gly | Ser | Gly | Ala | Gly | Ala | Gly | Ser | Gly | Ala | Ala | Arg | Tyr | Val | Val | Leu | |
| | | 35 | | | | | 40 | | | | | 45 | | | | |
| CCA | CGT | CCG | GTA | TGT | TTC | GAA | AAA | GCT | GCA | GGC | TAT | GGA | GCT | GGC | GCT | 192 |
| Pro | Arg | Pro | Val | Cys | Phe | Glu | Lys | Ala | Ala | Gly | Tyr | Gly | Ala | Gly | Ala | |
| | 50 | | | | | 55 | | | | | 60 | | | | | |
| GGC | TCA | GGT | GCT | GGA | GCA | GGA | AGC | GGA | GCG | | | | | | | 222 |
| Gly | Ser | Gly | Ala | Gly | Ala | Gly | Ser | Gly | Ala | | | | | | | |
| 65 | | | | | 70 | | | | | | | | | | | |

( 2 ) INFORMATION FOR SEQ ID NO:5:

( i ) SEQUENCE CHARACTERISTICS:
        ( A ) LENGTH: 74 amino acids
        ( B ) TYPE: amino acid
        ( D ) TOPOLOGY: linear ( i i ) MOLECULE TYPE: protein ( x i ) SEQUENCE DESCRIPTION: SEQ ID NO:5:

| | | | | | | | | | | | | | | |
|---|---|---|---|---|---|---|---|---|---|---|---|---|---|---|
| Gly | Ala | Gly | Ser | Gly | Ala | Gly | Ala | Gly | Ser | Gly | Ala | Gly | Ala | Gly | Ser |
| 1 | | | | 5 | | | | | 10 | | | | | 15 |
| Gly | Ala | Gly | Ala | Gly | Ser | Gly | Ala | Gly | Ala | Gly | Ser | Gly | Ala | Gly | Ala |
| | | | 20 | | | | | 25 | | | | | 30 | |
| Gly | Ser | Gly | Ala | Gly | Ala | Gly | Ser | Gly | Ala | Ala | Arg | Tyr | Val | Val | Leu |
| | | 35 | | | | | 40 | | | | | 45 | | |
| Pro | Arg | Pro | Val | Cys | Phe | Glu | Lys | Ala | Ala | Gly | Tyr | Gly | Ala | Gly | Ala |
| | 50 | | | | | 55 | | | | | 60 | | | |
| Gly | Ser | Gly | Ala | Gly | Ala | Gly | Ser | Gly | Ala | | | | | |
| 65 | | | | | 70 | | | | | | | | | |

( 2 ) INFORMATION FOR SEQ ID NO:6:

( i ) SEQUENCE CHARACTERISTICS:
        ( A ) LENGTH: 945 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:6:

| | | | | | | | | | | | | | | |
|---|---|---|---|---|---|---|---|---|---|---|---|---|---|---|
| Met | Asp | Pro | Val | Val | Leu | Gln | Arg | Arg | Asp | Trp | Glu | Asn | Pro | Gly | Val |
| 1 | | | | 5 | | | | | 10 | | | | | 15 | |
| Thr | Gln | Leu | Asn | Arg | Leu | Ala | Ala | His | Pro | Pro | Phe | Ala | Ser | Asp | Pro |
| | | | 20 | | | | | 25 | | | | | 30 | | |
| Met | Gly | Ala | Gly | Ser | Gly | Ala | Gly | Ala | Gly | Ser | Gly | Ala | Gly | Ala | Gly |
| | | | 35 | | | | | 40 | | | | | 45 | | |
| Ser | Gly | Ala | Gly | Ala | Gly | Ser | Gly | Ala | Gly | Ala | Gly | Ser | Gly | Ala | Gly |
| | | 50 | | | | | 55 | | | | | 60 | | | |
| Ala | Gly | Ser | Gly | Ala | Gly | Ala | Gly | Ser | Gly | Ala | Ala | Arg | Tyr | Val | Val |
| 65 | | | | | 70 | | | | | 75 | | | | | 80 |
| Leu | Pro | Arg | Pro | Val | Cys | Phe | Glu | Lys | Ala | Ala | Gly | Tyr | Gly | Ala | Gly |
| | | | | 85 | | | | | 90 | | | | | 95 | |
| Ala | Gly | Ser | Gly | Ala | Gly | Ala | Gly | Ser | Gly | Ala | Gly | Ala | Gly | Ser | Gly |
| | | | 100 | | | | | 105 | | | | | 110 | | |
| Ala | Gly | Ala | Gly | Ser | Gly | Ala | Gly | Ala | Gly | Ser | Gly | Ala | Gly | Ala | Gly |
| | | | 115 | | | | | 120 | | | | | 125 | | |

-continued

```
Ser Gly Ala Gly Ala Gly Ser Gly Ala Gly Ala Gly Ser Gly Ala Gly
    130                 135                 140
Ala Gly Ser Gly Ala Ala Arg Tyr Val Val Leu Pro Arg Pro Val Cys
145                 150                 155                 160
Phe Glu Lys Ala Ala Gly Tyr Gly Ala Gly Ala Gly Ser Gly Ala Gly
                165                 170                 175
Ala Gly Ser Gly Ala Gly Ala Gly Ser Gly Ala Gly Ala Gly Ser Gly
            180                 185                 190
Ala Gly Ala Gly Ser Gly Ala Gly Ala Gly Ser Gly Ala Gly Ala Gly
        195                 200                 205
Ser Gly Ala Gly Ala Gly Ser Gly Ala Gly Ala Gly Ser Gly Ala Ala
    210                 215                 220
Arg Tyr Val Val Leu Pro Arg Pro Val Cys Phe Glu Lys Ala Ala Gly
225                 230                 235                 240
Tyr Gly Ala Gly Ala Gly Ser Gly Ala Gly Ala Gly Ser Gly Ala Gly
                245                 250                 255
Ala Gly Ser Gly Ala Gly Ala Gly Ser Gly Ala Gly Ala Gly Ser Gly
            260                 265                 270
Ala Gly Ala Gly Ser Gly Ala Gly Ala Gly Ser Gly Ala Gly Ala Gly
        275                 280                 285
Ser Gly Ala Gly Ala Gly Ser Gly Ala Ala Arg Tyr Val Val Leu Pro
    290                 295                 300
Arg Pro Val Cys Phe Glu Lys Ala Ala Gly Tyr Gly Ala Gly Ala Gly
305                 310                 315                 320
Ser Gly Ala Gly Ala Gly Ser Gly Ala Gly Ala Gly Ser Gly Ala Gly
                325                 330                 335
Ala Gly Ser Gly Ala Gly Ala Gly Ser Gly Ala Gly Ala Gly Ser Gly
            340                 345                 350
Ala Gly Ala Gly Ser Gly Ala Gly Ala Gly Ser Gly Ala Gly Ala Gly
        355                 360                 365
Ser Gly Ala Ala Arg Tyr Val Val Leu Pro Arg Pro Val Cys Phe Glu
    370                 375                 380
Lys Ala Ala Gly Tyr Gly Ala Gly Ala Gly Ser Gly Ala Gly Ala Gly
385                 390                 395                 400
Ser Gly Ala Gly Ala Gly Ser Gly Ala Gly Ala Gly Ser Gly Ala Gly
                405                 410                 415
Ala Gly Ser Gly Ala Gly Ala Gly Ser Gly Ala Gly Ala Gly Ser Gly
            420                 425                 430
Ala Gly Ala Gly Ser Gly Ala Gly Ala Gly Ser Gly Ala Ala Arg Tyr
        435                 440                 445
Val Val Leu Pro Arg Pro Val Cys Phe Glu Lys Ala Ala Gly Tyr Gly
450                 455                 460
Ala Gly Ala Gly Ser Gly Ala Gly Ala Gly Ser Gly Ala Gly Ala Gly
465                 470                 475                 480
Ser Gly Ala Gly Ala Gly Ser Gly Ala Gly Ala Gly Ser Gly Ala Gly
                485                 490                 495
Ala Gly Ser Gly Ala Gly Ala Gly Ser Gly Ala Gly Ala Gly Ser Gly
            500                 505                 510
Ala Gly Ala Gly Ser Gly Ala Ala Arg Tyr Val Val Leu Pro Arg Pro
        515                 520                 525
Val Cys Phe Glu Lys Ala Ala Gly Tyr Gly Ala Gly Ala Gly Ser Gly
    530                 535                 540
Ala Gly Ala Gly Ser Gly Ala Gly Ala Gly Ser Gly Ala Gly Ala Gly
545                 550                 555                 560
```

```
Ser Gly Ala Gly Ala Gly Ser Gly Ala Gly Ala Gly Ser Gly Ala Gly
            565             570             575
Ala Gly Ser Gly Ala Gly Ala Gly Ser Gly Ala Gly Ala Gly Ser Gly
            580             585             590
Ala Ala Arg Tyr Val Val Leu Pro Arg Pro Val Cys Phe Glu Lys Ala
            595             600             605
Ala Gly Tyr Gly Ala Gly Ala Gly Ser Gly Ala Gly Ala Gly Ser Gly
            610             615             620
Ala Gly Ala Gly Ser Gly Ala Gly Ala Gly Ser Gly Ala Gly Ala Gly
625             630             635             640
Ser Gly Ala Gly Ala Gly Ser Gly Ala Gly Ala Gly Ser Gly Ala Gly
            645             650             655
Ala Gly Ser Gly Ala Gly Ala Gly Ser Gly Ala Ala Arg Tyr Val Val
            660             665             670
Leu Pro Arg Pro Val Cys Phe Glu Lys Ala Ala Gly Tyr Gly Ala Gly
            675             680             685
Ala Gly Ser Gly Ala Gly Ala Gly Ser Gly Ala Gly Ala Gly Ser Gly
            690             695             700
Ala Gly Ala Gly Ser Gly Ala Gly Ala Gly Ser Gly Ala Gly Ala Gly
705             710             715             720
Ser Gly Ala Gly Ala Gly Ser Gly Ala Gly Ala Gly Ser Gly Ala Gly
            725             730             735
Ala Gly Ser Gly Ala Ala Arg Tyr Val Val Leu Pro Arg Pro Val Cys
            740             745             750
Phe Glu Lys Ala Ala Gly Tyr Gly Ala Gly Ala Gly Ser Gly Ala Gly
            755             760             765
Ala Gly Ser Gly Ala Gly Ala Gly Ser Gly Ala Gly Ala Gly Ser Gly
            770             775             780
Ala Gly Ala Gly Ser Gly Ala Gly Ala Gly Ser Gly Ala Gly Ala Gly
785             790             795             800
Ser Gly Ala Gly Ala Gly Ser Gly Ala Gly Ala Gly Ser Gly Ala Ala
            805             810             815
Arg Tyr Val Val Leu Pro Arg Pro Val Cys Phe Glu Lys Ala Ala Gly
            820             825             830
Tyr Gly Ala Gly Ala Gly Ser Gly Ala Gly Ala Gly Ser Gly Ala Gly
            835             840             845
Ala Gly Ser Gly Ala Gly Ala Gly Ser Gly Ala Gly Ala Gly Ser Gly
            850             855             860
Ala Gly Ala Gly Ser Gly Ala Gly Ala Gly Ser Gly Ala Gly Ala Gly
865             870             875             880
Ser Gly Ala Gly Ala Gly Ser Gly Ala Ala Arg Tyr Val Val Leu Pro
            885             890             895
Arg Pro Val Cys Phe Glu Lys Ala Ala Gly Tyr Gly Ala Gly Ala Gly
            900             905             910
Ser Gly Ala Gly Ala Gly Ser Gly Ala Gly Ala Met Asp Pro Gly Arg
            915             920             925
Tyr Gln Leu Ser Ala Gly Arg Tyr His Tyr Gln Leu Val Trp Cys Gln
            930             935             940
Lys
945
```

( 2 ) INFORMATION FOR SEQ ID NO:7:

( i ) SEQUENCE CHARACTERISTICS:

(A) LENGTH: 45 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:7:

CCGGGTGCAT CGATCAAAGT AGCTGTTAGC GCCGGACCGT CTGCA  45

(2) INFORMATION FOR SEQ ID NO:8:

(i) SEQUENCE CHARACTERISTICS:
(A) LENGTH: 45 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:8:

ACGTGGCCCA CGTAGCTAGT TTCATCGACA ATCGCGGCCT GGCAG  45

(2) INFORMATION FOR SEQ ID NO:9:

(i) SEQUENCE CHARACTERISTICS:
(A) LENGTH: 228 base pairs
(B) TYPE: nucleic acid
(C) STRANDEDNESS: double
(D) TOPOLOGY: linear (ii) MOLECULE TYPE: cDNA (ix) FEATURE:
(A) NAME/KEY: CDS
(B) LOCATION: 1..228

(xi) SEQUENCE DESCRIPTION: SEQ ID NO:9:

| GGT | GCC | GGC | AGC | GGT | GCA | GGA | GCC | GGT | TCT | GGA | GCT | GGC | GCG | GGC | TCT | 48 |
| Gly | Ala | Gly | Ser | Gly | Ala | Gly | Ala | Gly | Ser | Gly | Ala | Gly | Ala | Gly | Ser | |
| 1 | | | | 5 | | | | | 10 | | | | | 15 | | |

| GGC | GCG | GGC | GCA | GGA | TCC | GGC | GCA | GGC | GCT | GGT | TCT | GGC | GCA | GGG | GCA | 96 |
| Gly | Ala | Gly | Ala | Gly | Ser | Gly | Ala | Gly | Ala | Gly | Ser | Gly | Ala | Gly | Ala | |
| | | 20 | | | | | 25 | | | | | 30 | | | | |

| GGC | TCT | GGC | GCA | GGA | GCG | GGG | TCT | GGA | GCT | GCA | CCG | GGT | GCA | TCG | ATC | 144 |
| Gly | Ser | Gly | Ala | Gly | Ala | Gly | Ser | Gly | Ala | Ala | Pro | Gly | Ala | Ser | Ile | |
| | | 35 | | | | | 40 | | | | | 45 | | | | |

| AAA | GTA | GCT | GTT | AGC | GCC | GGA | CCG | TCT | GCA | GGC | TAT | GGA | GCT | GGC | GCT | 192 |
| Lys | Val | Ala | Val | Ser | Ala | Gly | Pro | Ser | Ala | Gly | Tyr | Gly | Ala | Gly | Ala | |
| | 50 | | | | | 55 | | | | | 60 | | | | | |

| GGC | TCA | GGT | GCT | GGA | GCA | GGA | AGC | GGA | GCG | GGT | GCC | | | | | 228 |
| Gly | Ser | Gly | Ala | Gly | Ala | Gly | Ser | Gly | Ala | Gly | Ala | | | | | |
| 65 | | | | 70 | | | | | 75 | | | | | | | |

(2) INFORMATION FOR SEQ ID NO:10:

(i) SEQUENCE CHARACTERISTICS:
(A) LENGTH: 76 amino acids
(B) TYPE: amino acid
(D) TOPOLOGY: linear (ii) MOLECULE TYPE: protein (xi) SEQUENCE DESCRIPTION: SEQ ID NO:10:

| Gly | Ala | Gly | Ser | Gly | Ala | Gly | Ala | Gly | Ser | Gly | Ala | Gly | Ala | Gly | Ser |
| 1 | | | | 5 | | | | | 10 | | | | | 15 | |

| Gly | Ala | Gly | Ala | Gly | Ser | Gly | Ala | Gly | Ala | Gly | Ser | Gly | Ala | Gly | Ala |
| | | 20 | | | | | 25 | | | | | 30 | | | |

```
Gly Ser Gly Ala Gly Ala Gly Ser Gly Ala Ala Pro Gly Ala Ser Ile
        35                  40                  45

Lys Val Ala Val Ser Ala Gly Pro Ser Ala Gly Tyr Gly Ala Gly Ala
    50                  55                  60

Gly Ser Gly Ala Gly Ala Gly Ser Gly Ala Gly Ala
65                  70                  75
```

(2) INFORMATION FOR SEQ ID NO:11:

(i) SEQUENCE CHARACTERISTICS:
      (A) LENGTH: 1018 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:11:

```
Met Asp Pro Val Val Leu Gln Arg Arg Asp Trp Glu Asn Pro Gly Val
1               5                   10                  15

Thr Gln Leu Asn Arg Leu Ala Ala His Pro Pro Phe Ala Ser Asp Pro
            20                  25                  30

Met Gly Ala Gly Ser Gly Ala Gly Ala Gly Ser Gly Ala Gly Ala Gly
        35                  40                  45

Ser Gly Ala Gly Ala Gly Ser Gly Ala Gly Ala Gly Ser Gly Ala Gly
    50                  55                  60

Ala Gly Ser Gly Ala Gly Ala Gly Ser Gly Ala Ala Pro Gly Ala Ser
65                  70                  75                  80

Ile Lys Val Ala Val Ser Ala Gly Pro Ser Ala Gly Tyr Gly Ala Gly
            85                  90                  95

Ala Gly Ser Gly Ala Gly Ala Gly Ser Gly Ala Gly Ala Gly Ser Gly
            100                 105                 110

Ala Gly Ala Gly Ser Gly Ala Gly Ala Gly Ser Gly Ala Gly Ala Gly
            115                 120                 125

Ser Gly Ala Gly Ala Gly Ser Gly Ala Gly Ala Gly Ser Gly Ala Gly
            130                 135                 140

Ala Gly Ser Gly Ala Ala Pro Gly Ala Ser Ile Lys Val Ala Val Ser
145                 150                 155                 160

Ala Gly Pro Ser Ala Gly Tyr Gly Ala Gly Ala Gly Ser Gly Ala Gly
            165                 170                 175

Ala Gly Ser Gly Ala Gly Ala Gly Ser Gly Ala Gly Ala Gly Ser Gly
            180                 185                 190

Ala Gly Ala Gly Ser Gly Ala Gly Ala Gly Ser Gly Ala Gly Ala Gly
            195                 200                 205

Ser Gly Ala Gly Ala Gly Ser Gly Ala Gly Ala Gly Ser Gly Ala Ala
            210                 215                 220

Pro Gly Ala Ser Ile Lys Val Ala Val Ser Ala Gly Pro Ser Ala Gly
225                 230                 235                 240

Tyr Gly Ala Gly Ala Gly Ser Gly Ala Gly Ala Gly Ser Gly Ala Gly
            245                 250                 255

Ala Gly Ser Gly Ala Gly Ala Gly Ser Gly Ala Gly Ala Gly Ser Gly
            260                 265                 270

Ala Gly Ala Gly Ser Gly Ala Gly Ala Gly Ser Gly Ala Gly Ala Gly
            275                 280                 285

Ser Gly Ala Gly Ala Gly Ser Gly Ala Ala Pro Gly Ala Ser Ile Lys
            290                 295                 300
```

```
Val Ala Val Ser Ala Gly Pro Ser Ala Gly Tyr Gly Ala Gly Ala Gly
305             310             315                 320

Ser Gly Ala Gly Ala Gly Ser Gly Ala Gly Ala Gly Ser Gly Ala Gly
            325             330             335

Ala Gly Ser Gly Ala Gly Ala Gly Ser Gly Ala Gly Ala Gly Ser Gly
            340             345             350

Ala Gly Ala Gly Ser Gly Ala Gly Ala Gly Ser Gly Ala Gly Ala Gly
            355             360             365

Ser Gly Ala Ala Pro Gly Ala Ser Ile Lys Val Ala Val Ser Ala Gly
    370             375             380

Pro Ser Ala Gly Tyr Gly Ala Gly Ala Gly Ser Gly Ala Gly Ala Gly
385             390             395             400

Ser Gly Ala Gly Ala Gly Ser Gly Ala Gly Ala Gly Ser Gly Ala Gly
            405             410             415

Ala Gly Ser Gly Ala Gly Ala Gly Ser Gly Ala Gly Ala Gly Ser Gly
            420             425             430

Ala Gly Ala Gly Ser Gly Ala Gly Ala Gly Ser Gly Ala Ala Pro Gly
            435             440             445

Ala Ser Ile Lys Val Ala Val Ser Ala Gly Pro Ser Ala Gly Tyr Gly
    450             455             460

Ala Gly Ala Gly Ser Gly Ala Gly Ala Gly Ser Gly Ala Gly Ala Gly
465             470             475             480

Ser Gly Ala Gly Ala Gly Ser Gly Ala Gly Ala Gly Ser Gly Ala Gly
            485             490             495

Ala Gly Ser Gly Ala Gly Ala Gly Ser Gly Ala Gly Ala Gly Ser Gly
            500             505             510

Ala Gly Ala Gly Ser Gly Ala Ala Pro Gly Ala Ser Ile Lys Val Ala
            515             520             525

Val Ser Ala Gly Pro Ser Ala Gly Tyr Gly Ala Gly Ala Gly Ser Gly
    530             535             540

Ala Gly Ala Gly Ser Gly Ala Gly Ala Gly Ser Gly Ala Gly Ala Gly
545             550             555             560

Ser Gly Ala Gly Ala Gly Ser Gly Ala Gly Ala Gly Ser Gly Ala Gly
            565             570             575

Ala Gly Ser Gly Ala Gly Ala Gly Ser Gly Ala Gly Ala Gly Ser Gly
            580             585             590

Ala Ala Pro Gly Ala Ser Ile Lys Val Ala Val Ser Ala Gly Pro Ser
        595             600             605

Ala Gly Tyr Gly Ala Gly Ala Gly Ser Gly Ala Gly Ala Gly Ser Gly
            610             615             620

Ala Gly Ala Gly Ser Gly Ala Gly Ala Gly Ser Gly Ala Gly Ala Gly
625             630             635             640

Ser Gly Ala Gly Ala Gly Ser Gly Ala Gly Ala Gly Ser Gly Ala Gly
            645             650             655

Ala Gly Ser Gly Ala Gly Ala Gly Ser Gly Ala Ala Pro Gly Ala Ser
            660             665             670

Ile Lys Val Ala Val Ser Ala Gly Pro Ser Ala Gly Tyr Gly Ala Gly
            675             680             685

Ala Gly Ser Gly Ala Gly Ala Gly Ser Gly Ala Gly Ala Gly Ser Gly
            690             695             700

Ala Gly Ala Gly Ser Gly Ala Gly Ala Gly Ser Gly Ala Gly Ala Gly
            705             710             715             720

Ser Gly Ala Gly Ala Gly Ser Gly Ala Gly Ala Gly Ser Gly Ala Gly
            725             730             735
```

-continued

```
Ala Gly Ser Gly Ala Ala Pro Gly Ala Ser Ile Lys Val Ala Val Ser
        740             745                 750

Ala Gly Pro Ser Ala Gly Tyr Gly Ala Gly Ala Gly Ser Gly Ala Gly
        755             760                 765

Ala Gly Ser Gly Ala Gly Ala Gly Ser Gly Ala Gly Ala Gly Ser Gly
    770             775                 780

Ala Gly Ala Gly Ser Gly Ala Gly Ala Gly Ser Gly Ala Gly Ala Gly
785             790                 795                         800

Ser Gly Ala Gly Ala Gly Ser Gly Ala Gly Ala Gly Ser Gly Ala Ala
                805             810                         815

Pro Gly Ala Ser Ile Lys Val Ala Val Ser Ala Gly Pro Ser Ala Gly
            820             825                 830

Tyr Gly Ala Gly Ala Gly Ser Gly Ala Gly Ala Gly Ser Gly Ala Gly
        835             840                 845

Ala Gly Ser Gly Ala Gly Ala Gly Ser Gly Ala Gly Ala Gly Ser Gly
    850             855                 860

Ala Gly Ala Gly Ser Gly Ala Gly Ala Gly Ser Gly Ala Gly Ala Gly
865             870                 875                         880

Ser Gly Ala Gly Ala Gly Ser Gly Ala Ala Pro Gly Ala Ser Ile Lys
                885             890                         895

Val Ala Val Ser Ala Gly Pro Ser Ala Gly Tyr Gly Ala Gly Ala Gly
            900             905                 910

Ser Gly Ala Gly Ala Gly Ser Gly Ala Gly Ala Gly Ser Gly Ala Gly
        915             920                 925

Ala Gly Ser Gly Ala Gly Ala Gly Ser Gly Ala Gly Ala Gly Ser Gly
    930             935                 940

Ala Gly Ala Gly Ser Gly Ala Gly Ala Gly Ser Gly Ala Gly Ala Gly
945             950                 955                         960

Ser Gly Ala Ala Pro Gly Ala Ser Ile Lys Val Ala Val Ser Ala Gly
                965             970                 975

Pro Ser Ala Gly Tyr Gly Ala Gly Ala Gly Ser Gly Ala Gly Ala Gly
            980             985                 990

Ser Gly Ala Gly Ala Met Asp Pro Gly Arg Tyr Gln Leu Ser Ala Gly
        995             1000                1005

Arg Tyr His Tyr Gln Leu Val Trp Cys Lys
    1010            1015
```

( 2 ) INFORMATION FOR SEQ ID NO:12:

( i ) SEQUENCE CHARACTERISTICS:
    ( A ) LENGTH: 12 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:12:

```
Arg Lys Gln Ala Ala Ser Ile Lys Val Ala Val Ser
1               5               10
```